United States Patent [19]
Cheng et al.

[11] Patent Number: 5,610,314
[45] Date of Patent: Mar. 11, 1997

[54] PROCESS FOR PREPARING DIOXOLENONE DERIVATIVES USED FOR MAKING PRODRUG ESTERS AND INTERMEDIATES

[75] Inventors: Peter T. W. Cheng, Lawrenceville; Chong-Oing Sun, East Windsor; Michael A. Poss, Lawrenceville, all of N.J.

[73] Assignee: Bristol-Myers Squibb Company, Princeton, N.J.

[21] Appl. No.: 415,799

[22] Filed: Apr. 3, 1995

[51] Int. Cl.$^6$ .................................................. C07D 321/00
[52] U.S. Cl. ............................ 549/228; 549/229; 560/56; 560/174; 562/463; 562/577
[58] Field of Search ...................... 560/56, 174; 562/463, 562/577; 549/228, 229

[56] References Cited

FOREIGN PATENT DOCUMENTS 59-212488A 12/1984 Japan.

OTHER PUBLICATIONS

Hiyama, T. et al, "The Photochemistry of 4,5–Disubstituted 1,3–Dioxolen–2–ones", Bull. Chem. Society of Japan, vol. 45, 2797–2801 (1972).

Ikeda, S. et al, "Studies on Prodrugs. III. A Convenient and Practical Preparation of Ampicillin Prodrugs", Chem. Pharm. Bull. vol. 32(11), 4316–4322 (1984).

Sakamoto, F. et al, "Studies on Prodrugs. II. Preparation and Characterization of (5–Substituted 2–Oxo–1, 3–dioxolen–4–yl)methyl Esters of Ampicillin", Chem. Pharm. Bull. vol. 32(6) 2241–2248 (1984).

Ikeda, S. et al, "A Convenient and Practical Preparation of 4–Chloromethyl–5–methyl–1,3–dioxol–2–one", Chem. Pharm. Bull. vol. 36(1), 394–397 (1988).

Sakamoto, F. et al, "Studies on Prodrugs. VI. Preparation and Characterization of (5–Substituted 2–Oxo–1, 3–dioxol–4–yl)methyl Esters of Mecillinam", Chem. Pharm. Bull., vol. 35(2), 642–646 (1987).

Sakamoto, F. et al, "Studies on Prodrugs. IV. Preparation and Characterization of N–(5–Substituted 2–oxo–1, 3–dioxol–4–yl)methyl Norfloxacin", Chem. Pharm. Bull., vol. 33(11) 4870–4877 (1985).

Kawai, H. et al, "2–Oxo–1,3–dixoels as Specific Substrates for Measurement of Arylesterase Activity", Chem. Pharm. Bull., vol 39(6), 1422–1425 (1991).

Miyauchi, M. et al, "Studies on Penem and Carbapenem. II. An Improved Synthesis of Orally Active Penem Antibiotic (5–Methyl–2–oxo–1,3–dioxol–4–yl)methyl (5R, 6S)–2–(2–Fluoroethylthio)–6–[(1R)–1–hydroxyethyl] penem–3–carboxylate", Chem. Pharm. Bull., vol. 38(4) 1077–1078 (1990).

Saari, W. S. et al, "3–Hydroxy–α–methyltyrosine Progenitors: Synthesis and evaluation of Some (2–Oxo–1, 3–dioxol–4–yl)methyl Esters", J. Med. Chem. 27, 713–717, (1984).

Alpegiani, M. et al, "On the Preparation of 4–Hydroxymethyl–5–Methyl–1,3–Dioxol–2–One", Synthetic Communications, vol. 22(9), 1277–1282 (1992).

Fischer, H. J. et al, "Darstellung Einiger Dialkylsubstituierter Cycloaddition an Athylen", Tetrahedron Letters No. 17, pp. 1701–1704 (1972).

Stahlke, K.-R. et al, "Zur Photochemie ary–substituierter Vinylencarbonate" Liebigs Ann. Chem. 764, 116–124 (1972).

Primary Examiner—Melvyn I. Marquis
Attorney, Agent, or Firm—Burton Rodney

[57] ABSTRACT

A process is provided for preparing dioxolenone derivatives of the structure

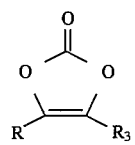

wherein R is alkyl or aryl and $R_3$ is $CO_2R_2$ (where $R_2$ is alkyl or arylalkyl such as benzyl, diphenylmethyl or para-methoxybenzyl). Intermediates produced in the above process are also provided as well as a method for preparing squalene synthetase inhibitors employing such intermediates.

11 Claims, No Drawings

PROCESS FOR PREPARING DIOXOLENONE DERIVATIVES USED FOR MAKING PRODRUG ESTERS AND INTERMEDIATES

FIELD OF THE INVENTION

The present invention relates to a process for preparing dioxolenone derivatives, such as alcohols or halides, which are employed in preparing prodrug esters of carboxylic acids, phosphonic acids and phosphinic acids, and to intermediates prepared in such process.

BACKGROUND OF THE INVENTION

Dioxolenone bromides of the structure

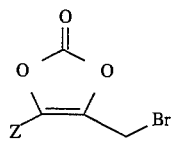

where Z is phenyl, methyl, t-butyl, or hydrogen, have been prepared by the bromination of dioxolenone starting materials of the structure

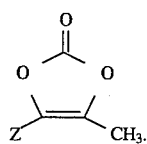

U.S. applications Ser. Nos. 266,888 and 266,843 (U.S. Pat. No. 5,470,845) each filed Jul. 5, 1994 (files Nos. HX59b and HX59c) disclose phosphonosulfonate squalene synthetase inhibitors of the structure

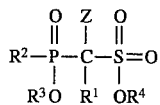

wherein $R^2$ is $OR^5$ or $R^{5a}$, $R^3$ and $R^5$ are independently H, alkyl, arylalkyl, aryl, cycloalkyl, metal ion or other pharmaceutically acceptable salt, or prodrug ester;

$R^{5a}$ is H, alkyl, arylalkyl or aryl;

$R^4$ is H, alkyl, aryl, cycloalkyl, arylalkyl, metal ion, or other pharmaceutically acceptable salt, or prodrug ester;

$R^1$ is a lipophilic group containing at least 7 carbons;

Z is H, halogen, lower alkyl or lower alkenyl.

The $R^1$ group is alkyl containing 7 to 25 carbons in the chain; alkenyl containing from 7 to 25 carbon atoms in the chain and from 1 to 6 double bonds; alkynyl containing 1 to 6 triple bonds; mixed alkenyl-alkynyl containing 1 to 5 double bonds and 1 to 5 triple bonds; or aryl; and where in the above groups alkenyl, alkynyl and/or aryl may be substituted or unsubstituted; cycloheteroalkyl linked through a carbon on the ring or a heteroatom; cycloalkyl; heteroarylalkyl; cycloalkylalkyl; heteroaryl; cycloheteroalkylalkyl; or a group of the structure

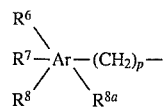

wherein Ar is aryl or heteroaryl, and Ar may include one to three additional rings fused to Ar, and wherein $(CH_2)_p$ contains from 1 to 15 carbons in the chain and may include 0, 1, 2 or 3 double bonds and/or 0, 1, 2 or 3 triple bonds in the normal chain, and may contain an ether or amino function in the chain, and/or may include 0, 1, 2 or 3 substituents as defined below for $R^6$; and $R^6$, $R^7$, $R^8$ and $R^{8a}$ are the same or different and are H, alkyl containing 1 to 40 carbons, alkoxy containing 1 to 40 carbons, alkenyl containing 2 to 40 carbons, alkenyloxy containing 2 to 40 carbons, alkynyl containing 2 to 40 carbons, alkynyloxy containing 2 to 40 carbons, hydroxy, halogen, nitro, amino, thiol, alkylthio, alkylsulfinyl, alkylsulfonyl, carboxy, alkoxycarbonyl, aminocarbonyl, alkylcarbonyloxy, alkylcarbonylamino, cycloheteroalkyl, cycloheteroalkylalkyl, heteroaryl, cycloalkyl, cycloalkylalkyl, Ar-alkyl, ArO, Ar-amino, Ar, Ar-thio, Ar-sulfinyl, Ar-sulfonyl, cyano, Ar-carbonyloxy, or Ar-carbonylamino.

The above applications disclose prodrug esters for the above compounds which are known in the art for both phosphorus and carboxylic acids. Examples of prodrug esters disclosed include the following:

(1-alkanoyloxy)alkyl such as,

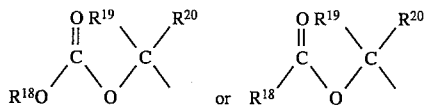

wherein $R^{18}$, $R^{19}$ and $R^{20}$ are H, alkyl, aryl or arylalkyl; however $R^{18}O$ cannot be HO. Examples of such prodrug esters include

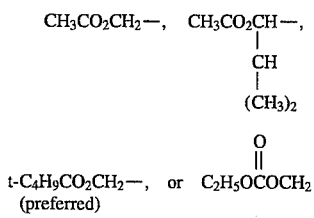

Other examples of prodrug esters disclosed include

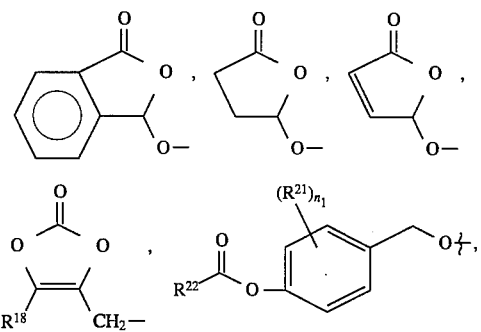

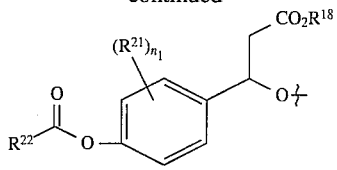

wherein $R^{18}$ can be H, alkyl (such as methyl or t-butyl), arylalkyl (such as benzyl) or aryl (such as phenyl); $R^{21}$ is H, alkyl, halogen or alkoxy, $R^{22}$ is alkyl, aryl, arylalkyl or alkoxyl, and $n_1$ is 0, 1 or 2; or $R^3$ and $R^5$ can be linked together as in

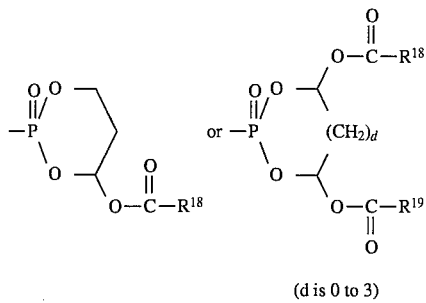

(d is 0 to 3)

U.S. application Ser. No. 295,121 filed Aug. 24, 1994, U.S. Pat. No. 5,447,922, discloses α-phosphonosulfinate squalene synthetase inhibitors having the structure

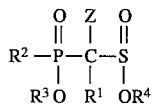

wherein $R^2$ is $OR^5$ or $R^{5a}$, $R^3$ and $R^5$ are independently H, alkyl, arylalkyl, aryl, cycloalkyl, metal ion or other pharmaceutically acceptable cation or salt;

$R^{5a}$ is alkyl, arylalkyl or aryl;

$R^4$ is H, metal ion, or other pharmaceutically acceptable cation or salt;

$R^1$ is a lipophilic group containing at least 7 carbons such as $Ar^1$—O—$Ar^2$ wherein $Ar^1$ is an aryl group, $Ar^2$ is an aryl group and p is 1 to 15; and Z is H, halogen, lower alkyl or lower alkenyl.

DESCRIPTION OF THE INVENTION

In accordance with the present invention, a process is provided for preparing a dioxolenone derivative of the structure I

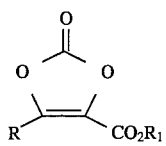

where R is alkyl or aryl, and $R_1$ is H, alkyl or arylalkyl (such as benzyl, para-methoxybenzyl or diphenylmethyl), which process includes the steps of subjecting an alcohol of the structure II

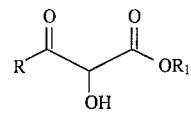

to dioxolenone formation by treating the alcohol with an amine base such as diisopropylethylamine, triethylamine, 4-methylmorpholine or pyridine, and a cyclizing agent such as phosgene or a phosgene equivalent such as diphosgene or triphosgene or 1,1'-carbonyldiimidazole, to form the dioxolenone derivative of the structure III

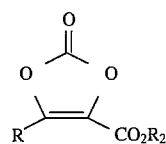

where $R_2$ is alkyl or arylalkyl such as benzyl, paramethoxybenzyl or diphenylmethyl (which is a novel compound).

The dioxolenone derivative III may optionally be reduced to form the corresponding acid IV

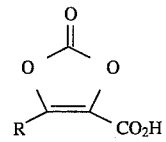

(which is a novel compound).

In addition, in accordance with the present invention, a process is provided for preparing a dioxolenone alcohol derivative of the structure V

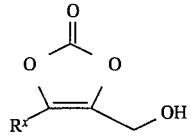

(which is a novel compound where $R^x$ is alkyl of 2 carbons or more excluding t-butyl (it is preferred that $R^x$ is 3 carbons or more), or aryl and is other than phenyl) which includes the steps of treating the dioxolenone acid derivative IV with a chlorination agent, preferably oxalyl chloride, thionyl chloride or phosphorus trichloride, to form the corresponding acid chloride, reducing the acid chloride by treating with a reducing agent, preferably tetrabutylammonium borohydride, lithium tri-tert-butoxyaluminohydride, or sodium borohydride, while cooling at a temperature within the range from about −78° to about 0° C., preferably about −78° C., to form the dioxolenone alcohol derivative V.

The dioxolenone alcohol derivative V may then be brominated by treating V with a bromination agent preferably carbon tetrabromide and an activating (or dehydrating) agent, preferably triphenylphosphine, at a temperature within the range from about 0° to about 25° C., to form the bromine derivative VI

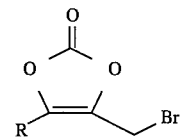

The dioxolenone moieties V and VI may be employed to form prodrug esters with various pharmaceutical compounds including various carboxylic acids, phosphonic acids and phosphinic acids to improve oral absorption of these drug moieties.

Examples of acid drug moieties which may be combined with the dioxolenone prodrug moiety V or VI include, but are not limited to ACE inhibitors such as enalapril, fosinopril, lisinopril, ramipril, quinapril or benazepril, angiotensin II receptor antagonists such as irbesartan, squalene synthetase inhibitors such as the phosphonosulfonates disclosed in U.S. applications Ser. Nos. 266,888 and 266,843 (U.S. Pat. No. 5,470,845), each filed Jul. 5, 1994, and α-phosphonosulfinates disclosed in U.S. application Ser. No. 295,121 filed Aug. 24, 1994, U.S. Pat. No. 5,447,922, all of which are incorporated herein by reference, beta-lactam antibiotics such as ampicillin, lenampicillin and mecillinam, antibacterial agents such as norfloxacin and nalidixic acid, nonsteroidal anti-inflammatory agents such as naproxen, ibuprofen and niflumic acid, antihypertensives and diuretics such as furosemide, anti-asthmatics such as cromoglycic acid, antihypertensives such as methyldopa, and antiviral agents such as 9-[2-(phosphonomethoxy)ethyl]adenine (PMEA).

Thus, in accordance with the present invention, a compound having improved oral absorption is provided having the structure

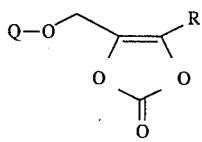

VIA where Q represents an acid drug moiety such as a drug moiety containing a carboxylic acid, a phosphonic acid or a phosphinic acid, such as an ACE inhibitor residue or an angiotensin II receptor antagonist residue or a squalene synthetase inhibitor residue or a residue of any of the other drugs set out hereinbefore, and R is alkyl or aryl.

In another aspect of the present invention, novel intermediates (for use in preparing prodrugs as described herein) are provided, which have the following formulae:

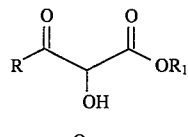

II

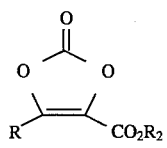

III

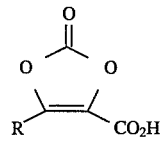

IV or

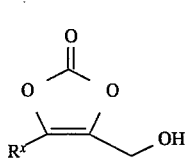

IVA where

R is alkyl or aryl;

$R_1$ is H, alkyl or arylalkyl, preferably benzyl, para-methoxybenzyl or diphenylmethyl;

$R_2$ is alkyl or arylalkyl, preferably benzyl, para-methoxybenzyl or diphenylmethyl, as well as para-nitrobenzyl, ortho-nitrobenzyl or triphenylmethyl; and $R^x$ is alkyl of at least 2 carbons, preferably of at least 3 carbons, such as n-propyl, i-propyl, n-butyl and t-butyl.

DETAILED DESCRIPTION OF THE INVENTION

In carrying out the preparation of dioxolenone ester derivative III, the alcohol II will be dissolved in a suitable inert organic solvent such as toluene, benzene, dichloromethane or tetrahydrofuran, cooled to a temperature within the range from about −78° to about 0° C., and then treated with an amine base, such as diisopropylethylamine, triethylamine, pyridine, N-methylmorpholine or N,N-dimethylaniline, preferably diisopropylethylamine, and a solution of cyclizing agent such as phosgene or a phosgene equivalent as set out above, in an organic solvent which is the same as or compatible with any of the solvents used for alcohol II.

The ratio of amine base to alcohol II to be employed will depend upon the cyclizing agent used. Thus, where the cyclizing agent employed is phosgene, diphosgene or triphosgene, the amine base will be employed in a molar ratio to alcohol II within the range from about 1:1 to about 5:1, preferably from about 2:1 to about 4:1; where 1,1'-carbonyldiimidazole is employed, the amine base will be employed in a molar ratio to alcohol II within the range from about 0.02 to about 0.5:1, preferably from about 0.03 to about 0.1:1.

Phosgene is employed in a molar ratio to alcohol II within the range from about 2:1 to about 9:1, preferably from about 6:1 to about 8:1. Triphosgene or 1,1'-carbonyldiimidazole is employed in a molar ratio to alcohol II within the range from about 1:1 to about 3:1, preferably from about 1.5:1 to about 2.5:1.

The dioxolenone ester derivative III may be reduced to the corresponding dioxolenone acid derivative IV by treating a solution of dioxolenone ester III in an inert organic solvent such as ethanol, ethyl acetate, THF or methanol, with hydrogen in the presence of a catalyst such as $Pd(OH)_2/C$, Raney Nickel, $PtO_2$ or Pd/C, preferably $Pd(OH)_2/C$, to form the acid IV.

The dioxolenone alcohol derivative V is prepared from acid IV by providing a solution of acid IV in an inert organic solvent such as methylene chloride or 1,2-dichloroethane, and cooling the solution to a temperature within the range from about 0° C. to about −20° C., preferably at 0° C. The cooled solution of acid IV is admixed with a catalytic amount of dimethylformamide, and then is treated with a chlorination agent such as oxalyl chloride, thionyl chloride or $PCl_3$, preferably oxalyl chloride, while maintaining the reaction mixture at a temperature within the range from about 0° to about 25° C., preferably at 25° C., to form the acid chloride of IV. The chlorination agent will be employed in a molar ratio to acid IV with the range from about 1.2:1 to about 1:1. The so-formed acid chloride is dissolved in an inert organic solvent such as methylene chloride, 1,2-dichloroethane or THF, and cooled to a temperature within the range from about −78° to about 0° C., preferably from about −78° to about −40° C., and is then treated with a reducing agent such as tetrabutylammonium borohydride, sodium borohydride or lithium tri-tert-butoxyaluminohydride, preferably tetrabutylammonium borohydride. The reaction mixture is stirred at a temperature within the range from about −78° to about 0° C., preferably from about −78° to about −40° C., to form the dioxolenone alcohol derivative V.

Preferably, when tetrabutylammonium borohydride is used as a reducing agent, the acid chloride of IV is dissolved in methylene chloride or 1,2-dichloroethane, cooled to from about −78° C. to about −40° C. and a solution of tetrabutylammonium borohydride in methylene chloride is added to the above cooled solution.

Preferably, when sodium borohydride is used as a reducing agent, a suspension of sodium borohydride in methylene chloride and ethanol is cooled at from about −78° C. to about −40° C., then a solution of acid chloride in methylene chloride is added dropwise to the above cooled suspension.

The corresponding brominated dioxolenone derivative VI is formed by treating a solution of dioxolenone alcohol derivative V in an inert organic solvent such as methylene chloride, 1,2-dichloroethane or chloroform, cooled to a temperature within the range from about 0° to about 25° C., with a brominating agent, such as carbon tetrabromide, phosphorus tribromide, bromine or N-bromosuccinimide/ dimethylsulfide, preferably carbon tetrabromide, and an activating/dehydrating agent such as triphenylphosphine, tributylphosphine, dimethylsulfide or triphenylphosphite, preferably triphenylphosphine.

The brominating agent is employed in a molar ratio to VI within the range from about 2:1 to about 1:1, preferably from about 1.2:1 to about 1.1:1, and the triphenylphosphine or other activating/dehydrating agent is employed in a molar ratio to VI within the range from about 2:1 to about 1:1, preferably from about 1.2:1 to about 1.1:1.

The starting alcohol II may be prepared by reacting an ester of the structure IIA

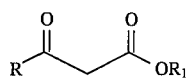

with a sulfonyl azide of the structure VII

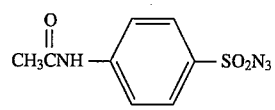

in the presence of a weak organic base to form an α-diazo β-keto ester of the structure VIII

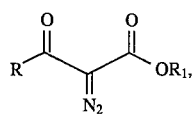

treating the α-diazo β-keto ester in an aqueous organic solvent (such at tetrahydrofuran or 1,4-dioxane) with catalytic amounts of a catalyst such as

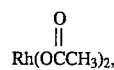

copper (metal) or copper chloride at a temperature within the range from about 60° to about 100° C., to form the alcohol of the structure II

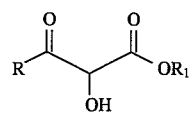

which is a novel compound where R is aryl or alkyl and $R_1$ is arylalkyl such as benzyl.

In addition, in accordance with the present invention, a process is provided for preparing a dioxolenone ester of a phosphonosulfonate (squalene synthetase inhibitor, as disclosed in U.S. applications Ser. Nos. 266,888 and 266,843, each filed Jul. 5, 1994, the latter being U.S. Pat. No. 5,470,845), or a phosphonosulfinate (squalene synthetase inhibitor as disclosed in application Ser. No. 295,121) wherein a phosphonosulfonate of the structure X

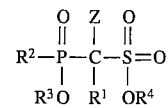

or a phosphonosulfinate of the structure XA

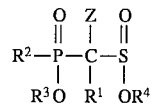

wherein $R^2$ is $OR^5$ or $R^{5a}$, $R^3$ and $R^5$ are independently H, alkyl, arylalkyl, aryl or cycloalkyl;

$R^{5a}$ is H, alkyl, arylalkyl or aryl;

$R^4$ is H, alkyl, aryl, cycloalkyl or arylalkyl;

$R^1$ is a lipophilic group containing at least 7 carbons;

Z is H, halogen, lower alkyl or lower alkenyl;

is treated with an amine base such as diisopropylethylamine, triethylamine, N-methylmorpholine or tributylamine, preferably diisopropylethylamine, in the presence of an inert organic solvent such as acetonitrile, N,N′-dimethyl-formamide and methylene chloride, and the so-formed solution is treated with dioxolenone bromide VI of the structure VI

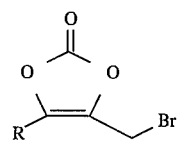

where R is alkyl or aryl, to form the ester of the structure XI

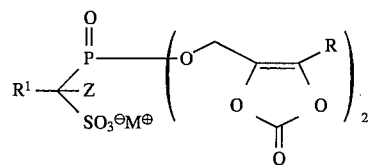

or

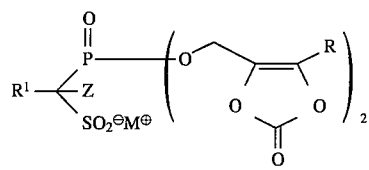

(XI and XIA are novel compounds) wherein $R^1$ is a lipophilic group and M is a metal ion as defined herein such as Na, Li or K, or $NH_4^+$.

The bromide VI will be employed in a molar ratio to the phosphonosulfonate X or phosphonosulfinate XA within the range from about 6:1 to about 2:1, preferably from about 4:1 to about 2:1, and the amine base will be employed in a molar ratio to phosphonosulfonate X or phosphonosulfinate XA within the range from about 6:1 to about 2:1, preferably from about 4:1 to about 3:1.

In the starting phosphonosulfonate X or phosphonosulfinate XA, the lipophilic group $R^1$ is alkyl containing 7 to 25 carbons in the chain; alkenyl containing from 7 to 25 carbon atoms in the chain and from 1 to 6 double bonds; alkynyl containing 7 to 25 carbons in the chain and from 1 to 6 triple bonds; mixed alkenyl-alkynyl containing 1 to 5 double bonds and 1 to 5 triple bonds; or aryl; and where in the above groups alkenyl, alkynyl and/or aryl may be substituted or unsubstituted; cycloheteroalkyl linked through a carbon on the ring or a heteroatom; cycloalkyl; heteroarylalkyl; cycloalkylalkyl; heteroaryl; cycloheteroalkylalkyl; or a group of the structure

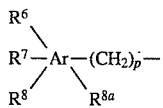

wherein Ar is aryl or heteroaryl, and Ar may include one to three additional rings fused to Ar, and wherein $(CH_2)_p$ contains from 1 to 15 carbons in the chain and may include 0, 1, 2 or 3 double bonds and/or 0, 1, 2 or 3 triple bonds in the normal chain, and may contain an ether or amino function in the chain, and/or may include 0, 1, 2 or 3 substituents as defined below for $R^6$; and $R^6$, $R^7$, $R^8$ and $R^{8a}$ are the same or different and are H, alkyl containing 1 to 40 carbons, alkoxy containing 1 to 40 carbons, alkenyl containing 2 to 40 carbons, alkenyloxy containing 2 to 40 carbons, alkynyl containing 2 to 40 carbons, alkynyloxy containing 2 to 40 carbons, hydroxy, halogen, nitro, amino, thiol, alkylthio, alkylsulfinyl, alkylsulfonyl, carboxy, alkoxycarbonyl, aminocarbonyl, alkylcarbonyloxy, alkylcarbonylamino, cycloheteroalkyl, cycloheteroalkylalkyl, heteroaryl, cycloalkyl, cycloalkylalkyl, Ar-alkyl, ArO, Ar-amino, Ar, Ar-thio, Ar-sulfinyl, Ar-sulfonyl, cyano, Ar-carbonyloxy, or Ar-carbonylamino.

In a preferred starting phosphonosulfonate X or phosphonosulfinate XA, $R^1$ is $Ar^1—O—A^2—(CH_2)_p—$, wherein $Ar^1$ is an aryl group and $Ar^2$ is an aryl group, and p is 1 to 15; and Z is H, halogen, lower alkyl or lower alkenyl.

Thus $R^1$ can be $Ar^1—O—Ar^2—(CH_2)_p—$ such as phenoxyphenylalkyl or phenoxyphenylalkenyl.

Examples of such $Ar^1—O—Ar^2—(CH_2)_p—$ groups include

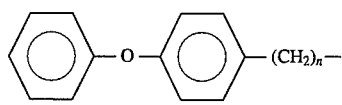

n is 2, 3 or 4, or

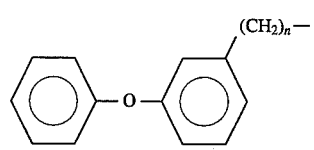

n is 2, 3 or 4, or

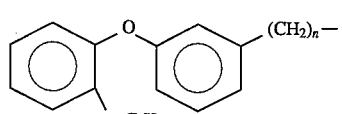

n is 2, 3 or 4, or

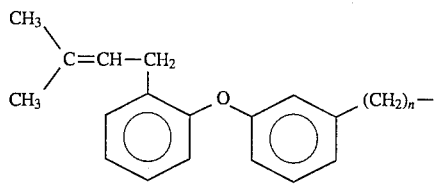

n is 2, 3 or 4, or

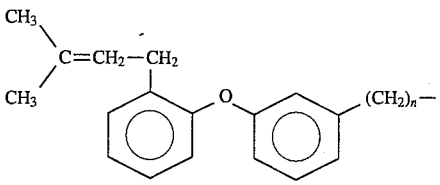

n is 2, 3 or 4.

Examples of starting phosphonosulfonate compounds X suitable for use herein include, but are not limited to 3-phenoxy-α-phosphonobenzenebutanesulfonic acid;
3-(2-propoxyphenoxy)-α-phosphonobenzenebutanoic acid;
α-phosphono-3-(2-propylphenoxy)benzenebutane sulfonic acid;
3-[2-(2-ethoxymethyl)phenoxy]-α-phosphonobenzenebutanesulfonic acid;
α-[bis[(2,2-dimethyl-1-oxopropoxy)methoxy]phosphinyl]-3-phenoxybenzenebutanesulfonic acid;
(S)-(−)-3-phenoxy-α-phosphonobenzenebutanesulfonic acid;
(R)-(+)-3-phenoxy-α-phosphonobenzenebutanesulfonic acid;
(R)-(−)-3-phenoxy-α-phosphonobenzenebutanesulfonic acid;
(S)-(+)-3-phenoxy-α-phosphonobenzenebutanesulfonic acid;
(S)-α-[bis[(2,2-dimethyl-1-oxopropoxy)methoxy]phosphinyl]-3-phenoxybenzenebutanesulfonic acid;
5-phenoxy-α-phosphono-2-thiophenebutanesulfonic acid.

A preferred starting phosphonosulfonate X has the formula

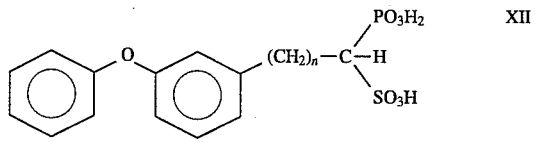    XII where n is 2, 3 or 4.

Examples of starting phosphonosulfinate compound XA suitable for use herein include compounds having the formula

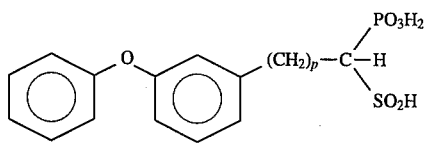

where p is 2, 3, 4 or 5 or an ester thereof, preferably 3-phenoxy-α-phosphonobenzenebutanesulfinic acid, or an ester thereof,

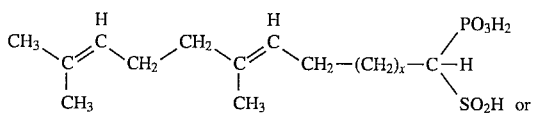

wherein x is 1 to 8 or

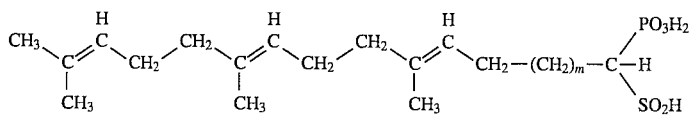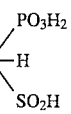

wherein m is 1 to 5;

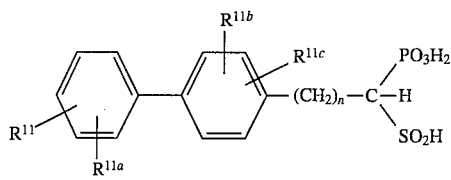

wherein n=1 to 15;
$R^{11}$, $R^{11a}$, $R^{11b}$, and $R^{11c}$ are independently selected from H, alkyl, halo, alkoxy, alkenyl;

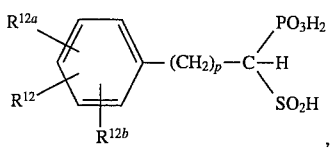

wherein $R^{12}$, $R^{12a}$ and $R^{12b}$ are independently selected from H, aryl, alkylphenyl, alkyl containing 1 to 20 carbons, halo, alkoxy, alkenyl, arylalkyloxy, alkenyloxy, aryloxy, phenylalkyl, alkylphenoxy, alkenylphenyl; or

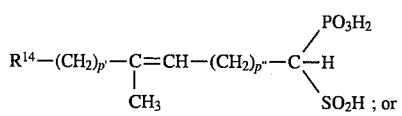

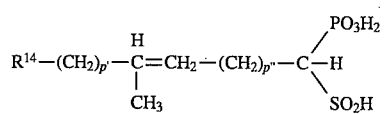

wherein $R^{14}$ is aryl, heteroaryl, aryloxy, heteroaryloxy, cycloalkyl, heterocycloalkyl, and p' and p" are independently 1 to 4; or a pharmaceutically acceptable salt thereof, an ester thereof or a mixed ester-salt thereof.

Unless otherwise indicated, the term "lower alkyl" or "alkyl" as employed herein alone or as part of another group includes both straight and branched chain hydrocarbons, containing 1 to 40 carbons, preferably 1 to 20 carbons, in the normal chain, more preferably 1 to 12 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including 1 to 4 substituents such as F, Br, Cl or I or $CF_3$, alkoxy, aryl, arylalkyl, alkenyl, cycloalkyl, amino, hydroxy, alkylamido, alkanoylamino, arylcarbonylamino, nitro, cyano, thiol and/or alkylthio, as well as any of the other substituents as defined for $R^6$.

Unless otherwise indicated, the term "cycloalkyl" as employed herein alone or as part of another group includes saturated or partially unsaturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl, cyclododecyl and cyclohexenyl, any of which groups may be substituted with 1 to 4 substituents such as halogen, alkyl, alkoxy, hydroxy, aryl, arylalkyl, cycloalkyl, alkylamido, alkanoylamino, arylcarbonylamino, amino, nitro, cyano, thiol and/or alkylthio, as well as any of the other substituents as defined for $R^6$.

Unless otherwise indicated, the term "aryl" as employed herein refers to monocyclic or bicyclic aromatic groups containing from 6 to 10 carbons in the ring portion, such as phenyl, naphthyl, or phenyl or naphthyl substituted with 1 to 4 substituents such as alkyl, halogen (Cl, Br or F), alkoxy, hydroxy, amino, alkanoylamino, arylcarbonylamino, aryl, arylalkyl, cycloalkyl, alkylamido, nitro, cyano, thiol and/or alkylthio, as well as any of the other substituents as defined for $R^6$.

The term "aralkyl", "aryl-alkyl" or "aryl-lower alkyl" as used herein alone or as part of another group refers to alkyl groups as discussed above having an aryl substituent, such as benzyl or phenethyl, or naphthylpropyl.

The term "lower alkoxy", "alkoxy", "aryloxy" or "aralkoxy" as employed herein alone or as part of another group includes any of the above alkyl, aralkyl or aryl groups linked to an oxygen atom.

The term "lower alkylthio", alkylthio", "arylthio" or "aralkylthio" as employed herein alone or as part of another group includes any of the above alkyl, aralkyl or aryl groups linked to a sulfur atom.

The term "lower alkylamino", "alkylamino", "arylamino", or "arylalkylamino" as employed herein alone or as part of another group includes any of the above alkyl, aryl or arylalkyl groups linked to a nitrogen atom.

The term "alkanoyl" as used herein alone or as part of another group refers to alkyl linked to a carbonyl group.

Unless otherwise indicated, the term "lower alkenyl" or "alkenyl" as used herein by itself or as part of another group refers to straight or branched chain radicals of 2 to 40 carbons, preferably 3 to 30 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, alkyl, alkoxy, alkenyl, alkynyl, aryl, arylalkyl, cycloalkyl, amino, hydroxy, alkanoylamino, alkylamido, arylcarbonylamino, nitro, cyano, thiol and/or alkylthio, as well as any of the other substituents as defined for $R^6$.

Unless otherwise indicated, the term "lower alkynyl" or "alkynyl" as used herein by itself or as part of another group refers to straight or branched chain radicals of 2 to 40 carbons, preferably 2 to 20 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like, and which may be optionally substituted with 1 to 4 substituents, namely, halogen, alkyl, alkoxy, alkenyl, alkynyl, aryl, arylalkyl, cycloalkyl, amino, hydroxy, alkanoylamino, alkyl-amido, arylcarbonylamino, nitro, cyano, thiol, and/or alkylthio, as well as any of the other substituents as defined for $R^6$.

Examples of suitable $(CH_2)_p$ groups include

—CH=CH—CH$_2$—, —CH$_2$CH=CH—, —C≡C—CH$_2$—,

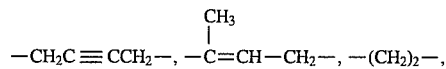

—(CH$_2$)$_3$—, —(CH$_2$)$_4$—, —(CH$_2$)$_2$—C(CH$_3$)$_2$—CH$_2$CH$_2$—,

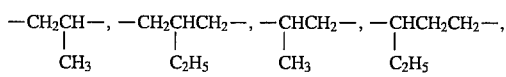

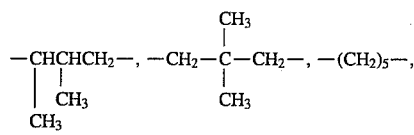

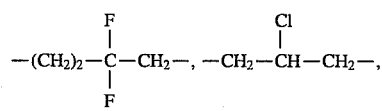

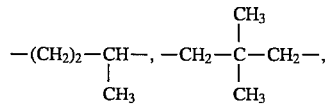

—CH(OH)—CH$_2$CH$_2$—, —CH(OCH$_3$)—CH$_2$CH$_2$, —CH$_2$OCH$_2$—,

—OCH$_2$CH$_2$—, —CH$_2$NHCH$_2$—, —NHCH$_2$CH$_2$—,

—CH$_2$—N(CH$_3$)—CH$_2$—, or —N(CH$_3$)—CH$_2$CH$_2$—.

The term "halogen" or "halo" as used herein refers to chlorine, bromine, fluorine, and iodine as well as CF$_3$, with chlorine or fluorine being preferred.

The term "amino" as used herein refers to unsubstituted amino as well as monosubstituted amino or disubstituted amino wherein the substituents may be alkyl and/or aryl.

The term "metal ion" refers to alkali metal ions such as sodium, potassium or lithium and alkaline earth metal ions such as magnesium and calcium, as well as zinc and aluminum.

The term "cycloheteroalkyl" as used herein as an $R^1$ substituent refers to a 5-, 6- or 7-membered saturated ring which includes 1 to 2 hetero atoms such as nitrogen, oxygen and/or sulfur, linked to the carbon "C" of

through a carbon atom or a heteroatom, where possible, optionally via the linker $(CH_2)_p$ (which is defined above), such as

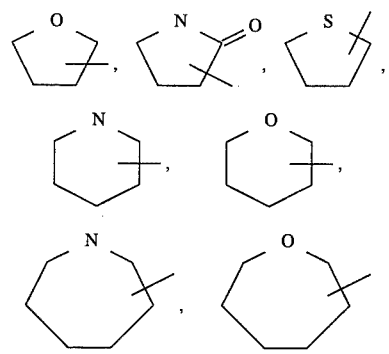

and the like. The above groups may include 1 to 3 substituents such as any of the $R^6$ groups as defined above. In addition, any of the above rings can be fused to a cycloalkyl, aryl, heteroaryl or cycloheteroalkyl ring.

The term "heteroaryl" as an $R^1$ substituent refers to a 5- or 6-membered aromatic ring which includes 1, 2, 3 or 4 hetero atoms such as nitrogen, oxygen or sulfur, which is linked to the carbon "C" of

through a carbon atom or a heteroatom, where possible, optionally via the linker $(CH_2)_p$ (which is defined above), such as

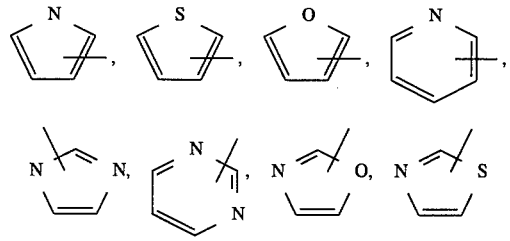

and the like. The above groups may include 1 to 3 substituents such as any of the $R^6$ groups as defined above. In addition, any of the above rings can be fused to a cycloalkyl, aryl, heteroaryl or cycloheteroalkyl ring.

The term "cycloheteroalkylalkyl" as defined by $R^1$ refers to cycloheteroalkyl groups as defined above linked through a C atom or heteroatom to the "C" of the

group through a $(CH_2)_p$ chain wherein p is preferably 1 to 8.

The term "heteroarylalkyl" as defined by $R^1$ refers to a heteroaryl group as defined above linked through a C atom or heteroatom to the "C" of

through a —(CH$_2$)$_p$— chain as defined above, where p is preferably 1 to 8.

The phosphonosulfonate prodrug esters XI and phosphonosulfinate prodrug esters XIA may be employed to inhibit cholesterol biosynthesis by inhibition of de novo squalene production. The phosphonosulfonate prodrug esters XI and phosphonosulfinate prodrug esters XIA inhibit the squalene synthetase enzyme and, in addition, some of the compounds of Formulae XI and XIA inhibit other enzymes in the pathway from isopentenyl diphosphate to squalene, that is, farnesyl diphosphate synthetase and isopentenyl diphosphate-dimethylallyl diphosphate isomerase.

The phosphonosulfonate prodrug esters XI and phosphonosulfinate prodrug esters XIA are useful in treating hyperlipoproteinemia, hyperlipidemia, hypercholesterolemia, hypertriglyceridemia, combined hypercholesterolemia and hypertriglyceridemia, and/or in preventing development of and/or treating atherosclerosis. Thus, the phosphonosulfonate prodrug esters XI and phosphonosulfinate prodrug esters XIA may be used to treat diseases such as chylomicronemia syndrome, Type I hyperlipoproteinemia, familial combined hyperlipoproteinemia, familial hypertriglyceridemia, mixed hyperlipoproteinemia, familial hypercholesterolemia and Type III hyperlipoproteinemia and/or atherosclerosis.

In addition, the phosphonosulfonate prodrug esters xI and phosphonosulfinate prodrug esters XIA may increase plasma high density lipoprotein cholesterol levels.

The phosphonosulfonate prodrug esters XI and phosphonosulfinate prodrug esters XIA may also be useful in inhibiting formation of gallstones, treating hepatitis D (by virtue of protein prenyltransferase inhibition, Glenn et al, Science, Vol. 256, pp. 1331–1333, May 29, 1992), treating tumors, lowering blood pressure, lowering blood sugar, treating diabetes mellitus, treating inflammation, as a diuretic, as an inotropic agent, as an anti-arthritic (antirheumatic) agent, in treating other diseases of calcium and phosphate metabolism including treatment of bone resorption, Paget's disease, osteoporosis, calcification of joints, implants and metastasis, as antitartar and anticalculus agents in toothpastes and mouthwashes, treating various stones and calculi, treating sickle cell anemia, treating hypoxia and ischemic tissue, and as an anti-ameobal agent, as well as for use in complexes with technetium-99m and radioiodinated derivatives for use as diagnostics.

The phosphonosulfonate prodrug esters XI and phosphonosulfinate prodrug esters XIA may also be employed in combination with an antihyperlipoproteinemic agent, hypocholesterolemic agent, and/or hypotriglyceridemic agent, and/or antiatherosclerotic agent such as one or more HMG CoA reductase inhibitors, for example, pravastatin, lovastatin, simvastatin, velostatin, fluvastatin, rivastatin, compactin, SDZ-63,370 (Sandoz), CI-981 (W-L), HR-780, L-645, 164, CL-274,471, dalvastatin, α-, β-, and γ-tocotrienol, (3R,5S,6E)-9,9-bis(4-fluorophenyl)-3,5-dihydroxy-8-(1-methyl-1H-tetrazol-5-yl)-6,8-nonadienoic acid, L-arginine salt, (S)-4-[[2-[4-(4-fluorophenyl)-5-methyl-2-(1-methylethyl)-6-phenyl-3-pyridinyl]ethenyl]hydroxyphosphinyl]-3-hydroxybutanoic acid, disodium salt, BB-476, (British Biotechnology), dihydrocompactin, [4R-[4α,6β(E)]]-6-[2-[5-(4-fluorophenyl)-3-(1-methylethyl)-1-(2-pyridinyl)-1H-pyrazol-4-yl]ethenyl]tetrahydro-4-hydroxy-2H-pyran-2-one, and/or 1H-pyrrole-1-heptanoic acid, 2-(4-fluorophenyl)-β,δ-dihydroxy-5-(1-methylethyl)-3-phenyl-4-[(phenylamino)carbonyl]calcium salt[R-(R*,R*)]; one or more fibric acid derivatives such as clofibrate, bezafibrate, Lopid(gemfibrozil) one or more other cholesterol biosynthesis inhibitors, such as NB-598, N-(1-oxododecyl)-4α,10-dimethyl-8-aza-trans-decal-3β-ol, 2,4-undecadienoic acid, 11-[3-(hydroxymethyl)-4-oxo-2-oxetanyl]-3,5,7-trimethyl-, [2R-[2α(2E,4E,7R*),3β]]; one or more bile acid sequestrants, for example, cholestyramine, colestipol, polidexide (DEAE-Sephadex); one or more antioxidants, for example probucol and Vitamin E; and/or one or more other lipid lowering and/or antiatherosclerotic agents, for example nicotinic acid or derivatives thereof, neomycin, p-aminosalicylic acid, probucol, hydroxy-propylmethylcellulose, LS-2904, ethanol, 2-[[1-methyl-2-[3-(trifluoromethyl)phenyl]ethyl]amino]benzoate (ester).

The above compounds to be employed in combination with the prodrug esters XI and XIA squalene synthetase inhibitor will be used in amounts as indicated in the Physicians' Desk Reference (PDR).

The phosphonosulfonate prodrug ester XI or phosphonosulfinate prodrug esters XIA will be employed in association with a pharmaceutical vehicle or diluent. The pharmaceutical composition can be formulated employing conventional solid or liquid vehicles or diluents and pharmaceutical additives of a type appropriate to the mode of desired administration. The composition can be administered to mammalian species including humans, monkeys, dogs, etc., by an oral route, for example, in the form of tablets, capsules, granules or powders, or they can be administered by a parenteral route in the form of injectable preparations. The dose for adults is preferably between 200 and 2,000 mg per day, of phosphonosulfonate prodrug ester or phosphonosulfinate prodrug ester squalene synthetase inhibitor which can be administered in a single dose or in the form of individual doses from 1–4 times per day.

A typical capsule for oral administration contains phosphonosulfonate prodrug ester or phosphonosulfinate prodrug ester (250 mg), lactose (75 mg) and magnesium stearate (15 mg). The mixture is passed through a 60 mesh sieve and packed into a No. 1 gelatin capsule.

A typical injectible preparation is produced by asceptically placing 250 mg of sterile phosphonosulfonate prodrug ester or phosphonosulfinate prodrug ester into a vial, asceptically freeze-drying and sealing. For use, the contents of the vial are mixed with 2 mL of physiological saline, to produce an injectible preparation.

The following Examples represent preferred embodiments of the present invention.

EXAMPLE 1

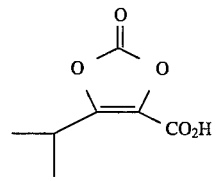

A.

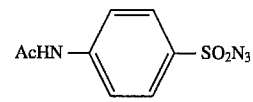

A suspension of p-acetamidobenzenesulfonyl chloride (Fluka, 100.0 g, 0.428 moles) in acetone (860 mL) was treated with sodium azide (Aldrich, 33.39 g, 0.514 moles, 1.2 eq) in water (260 mL). The solution was stirred overnight at room temperature under argon. The reaction mixture was divided into 3 portions and added to 1.5 L of water in 2 L Erlenmeyer flasks and stirred for 2 hours. Precipitates were collected by filtration and dried in vacuo over $P_2O_5$ to yield 81.1 g (79%) of title compound in the form of a white powder.

B.

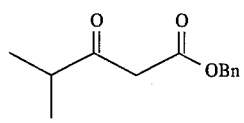

To a solution of ethyl isobutyryl acetate (10 g, 63.29 mmol) in toluene (180 mL) was added benzyl alcohol (Aldrich, 65 mL, 10 eq) followed by 4-dimethylaminopyridine (Aldrich, 1.0 g, 8.2 mmol, 0.13 eq). The mixture was refluxed for 44 hours and allowed to cool to room temperature. The reaction mixture was diluted with hexane (0.5 L), washed with 5% $KHSO_4$ (2 times), $H_2O$ (2 times), brine, dried over $Na_2SO_4$, filtered and concentrated to give a yellow oil, which was distilled under reduced pressure to afford 13.27 g (82%) of title compound. b.p.=120° C./2 mm; $^1H$ NMR and $^{13}C$ NMR ($CDCl_3$, 300, 75 MHz).

C.

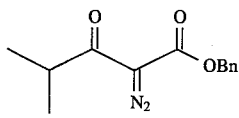

To a solution of Part B compound (13.20 g, 59.92 mmol) and Part A sulfonyl azide (14.40 g, 59.92 mmol) in $CH_3CN$ (500 mL) cooled to 0° C. was added distilled triethylamine (24.95 mL, 179.76 mmol, 3 eq) in one portion. The resultant yellow suspension was stirred at 0° C. for 30 minutes then at room temperature for 4 hours. The reaction was concentrated and triturated with 2:1 ethyl ether:petroleum ether (2×300 mL). The filtrate was concentrated and triturated again with 1:1 ethyl ether:petroleum ether (200 mL). The filtrate was concentrated and dried in vacuo affording 14.97 g of title compound as a yellow oil. $^1H$ NMR and $^{13}C$ NMR ($CDCl_3$, 270, 68 MHz), TLC: $R_f$=0.26 silica gel, 10% EtOAc in hexanes, UV and PMA detection.

D.

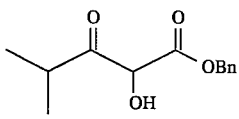

To a solution of Part C compound (14.89 g, ~60.45 mmol) in 2:1 THF:water (450 mL) was added rhodium(II) acetate dimer (Aldrich, 195 mg, 0.441 mmol, 0.007 eq) in one portion and the pale green solution was refluxed for 5.5 hours. The reaction mixture was concentrated in vacuo and the residue extracted with EtOAc (2×250 mL). The combined extracts were washed with brine (2×250 mL), dried over $Na_2SO_4$, filtered, and concentrated, and dried in vacuo to give 14.56 g of title compound as a yellow oil. $^1H$ NMR and $^{13}C$ NMR ($CDCl_3$, 300, 75 MHz), TLC: $R_f$=0.37 silica gel, 3:7 EtOAc:hexanes, UV and PMA detection.

E.

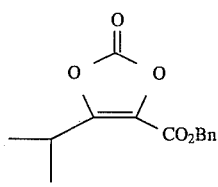

A solution of Part D compound (~59.92 mmol) in toluene (400 mL) cooled to 0° C. was treated with diisopropylethylamine (Aldrich, 72.5 mL, 419.4 mmol, 7 eq) followed by dropwise addition of 1.9M solution of phosgene in toluene (93.1 mL, 179.8 mmol, 3 eq) over 20 minutes. The resultant solution was stirred for 30 minutes at 0° C. and then at room temperature overnight. The reaction mixture was diluted with EtOAc (400 mL), washed with 5% $KHSO_4$ (2×200 mL), water (200 mL), brine, dried over $Na_2SO_4$, filtered, concentrated and absorbed onto Celite and purified on a 7×25 cm silica gel column eluting with 10% EtOAc in hexanes (5 L). Desired fractions were combined, concentrated, and dried in vacuo affording 10.77 g of title compound which was recrystallized from hot hexane. White crystals were collected by filtration and dried in vacuo to give 5.66 g of title compound. TLC: $R_f$=0.51 silica gel, 3:7 EtOAc:hexanes, UV and PMA detection.

Mass Spec: (CI); (M+$NH_4$) @ 280.

IR: (KBr) 3432, 2944, 1832, 1821, 1719, 1408, 1354, 1323, 1150, 1136, 1067, 754, 696 cm$^{-1}$.

$^1H$-NMR: 300 MHz; $CDCl_3$: δ1.25 (d, 6H, J=7.0 Hz), 3.50 (m, 1), 5.32 (s, 2H), 7.40 (m, 5H).

$^{13}C$-NMR: 75 MHz; $CDCl_3$: δ156.7, 151.0, 134.5, 128.7, 128.6, 128.5, 127.7, 67.3, 25.1, 19.4.

Anal. Calcd for $C_{14}H_{14}O_5$: C, 64.12; H, 5.38 Found: C, 64.06; H, 5.28.

The mother liquor (5 g) was purified on a 7×25 cm silica gel column eluting with 10% EtOAc in hexanes (4 L). Desired fractions were combined, concentrated, and dried in vacuo affording 2.32 g of title compound. $^1H$ NMR and $^{13}C$ NMR ($CDCl_3$, 300, 75 MHz); total 7.98 g; 51% overall yield from Part B compound.

F.

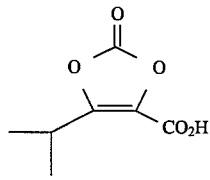

To a solution of Part E compound (7.98 g, 30.42 mmol) in EtOH (250 mL) was added Pd(OH)$_2$/C (Aldrich, 500 mg), and hydrogenated under a hydrogen balloon for 1 hour. The reaction mixture was filtered through a plug of Celite on a Millipore (45 µm nylon) filter. The filtrate was concentrated, stripped with $CH_2Cl_2$/toluene and dried in vacuo to yield 5.05 g of title compound as a yellow green solid. $^1H$ NMR and $^{13}C$ NMR ($CDCl_3$, 300 MHz, 75 MHz).

EXAMPLE 2

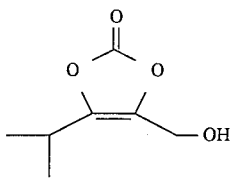

To a solution of Example 1 compound (5.05 g, 29.34 mmol) in $CH_2Cl_2$ (150 mL) cooled to 0° C. was treated with anhydrous DMF (Aldrich Sure Seal, 350 μL) followed by dropwise addition of oxalyl chloride (Aldrich, 2.82 mL, 32.27 mmol, 1.1 eq). The reaction was stirred at 0° C. for 25 minutes then at room temperature for one hour. The reaction mixture was concentrated in vacuo, stripped with $CH_2Cl_2$/toluene (2 times) and dried in vacuo for one hour to give the acid chloride.

The above acid chloride (~29 mmol) was dissolved in $CH_2Cl_2$ (150 mL) cooled to −78° C. and treated with a solution of tetrabutylammonium borohydride (Aldrich, 8.30 g, 32.27 mmol, 1.1 eq) in $CH_2Cl_2$ (50 mL) over 15 minutes and stirred at −78° C. for one hour and quenched with 0.1N HCl (70 mL). The reaction mixture was allowed to warm to room temperature, concentrated in vacuo and the residue was diluted with EtOAc (200 mL) and water (50 mL) and the layers separated. The aqueous layer was saturated with NaCl and extracted with EtOAc (2×100 mL). The combined EtOAc extracts were washed with brine (2×200 mL), dried over $Na_2SO_4$, filtered, and concentrated to afford 9.5 g crude yellow oil. The residue was purified on a 5×10 cm silica gel column eluting with 8:2 EtOAc:hexanes (1 L). The desired fractions were combined, concentrated, and dried in vacuo to afford 3.98 g (86% from Example 1 Part E compound) of title compound as a yellow oil. $^1H$ NMR and $^{13}C$ NMR ($CDCl_3$, 300, 75 MHz).

EXAMPLE 3

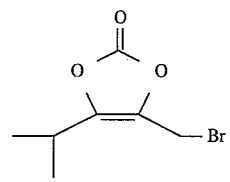

To a solution of Example 2 compound (3.945 g, 24.94 mmol) in $CH_2Cl_2$ (150 mL) cooled to 0° C. was added carbon tetrabromide (Aldrich, 9.93 g, 29.93 mmol, 1.2 eq) in one portion followed by triphenylphosphine (Aldrich, 7.20 g, 27.43 mmol, 1.1 eq) in one portion. The reaction was stirred at 0° C. for 30 minutes, concentrated, adsorbed onto Celite and purified on a 5×25 cm silica gel column eluting with 10% EtOAc in hexanes (3 L). The desired fractions were combined, concentrated, and dried in vacuo to afford 4.74 g (86%) of title compound as a yellow liquid. TLC: $R_f$=0.60 silica gel, 1:1 EtOAc:hexanes, UV and PMA detection.

Mass Spec: (CI); (M+$NH_4$) @ 238.

IR: ($CH_2Cl_2$ Film); 2976, 1827, 1470, 1314, 1250, 1194, 1063, 770, 654 $cm^{-1}$.

$^1$H-NMR: 300 MHz; $CDCl_3$: δ1.26 (d, 6H, J=6.9 Hz), 2.87 (m, 1), 4.22 (s, 2H).

$^{13}$C-NMR: 75 MHz; $CDCl_3$: δ153.0, 145.6, 132.8, 24.9, 19.6, 18.0.

Anal. Calc'd for $C_7H_9O_3Br$: C, 38.04; H, 4.10; Br, 36.15 Found: C, 38.28; H, 4.07; Br, 36.43.

HPLC: Rt=16.1 min (86%, UV 215); EM Lichrosphere select B (C-8, 5 m, 5×250 mm) 28–70% B:A (B=95% $CH_3CN$/5% $H_2O$+0.01M $NH_4OAc$, pH 5.5; A=95% $H_2O$/5% $CH_3CN$+0.01M $NH_4OAc$, pH 5.5), 1 mL/minute.

EXAMPLE 4

α-[Bis[[5-(1-methylethyl)-2-oxo-1,3-dioxol-4-yl]methoxy]phosphinyl]-3-phenoxybenzenebutanesulfonic acid, ammonium salt

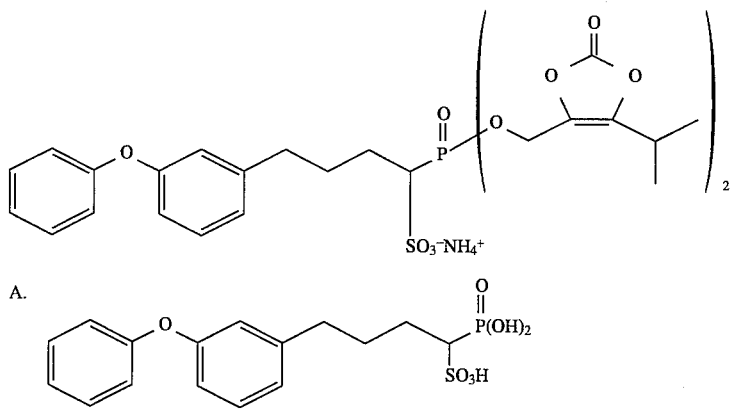

The Part A triacid compound was prepared as described in U.S. application Ser. No. 266,888, filed Jul. 5, 1994. The triacid was azeotroped with EtOAc/toluene (3x's) and dried in vacuo overnight to give a clear reddish oil.

B. α-[Bis[[5-(1-methylethyl)-2-oxo-1,3-dioxol-4-yl]-methoxy]phosphinyl]-3-phenoxybenzenebutanesulfonic acid, ammonium salt To a solution of Part A triacid (747 mg, 1.93 mmol) in $CH_3CN$ (Aldrich Sure Seal, 15 mL) was added dropwise diisopropylethylamine (Fluka, 1.27 mL, 7.34 mmol, 3.8 eq) followed by dropwise addition of the Example 3 bromide (1.62 g, 7.34 mmol, 3.8 eq). The reaction was stirred for 100 hrs while monitoring the ratio of product formation versus Example 3 bromide by HPLC. The reaction was diluted with EtOAc (50 mL) and washed with 5% potassium phosphate monobasic pH 2 buffer (3×40 mL). The combined aqueous phases were extracted with EtOAc (2×25 mL). The combined EtOAc extracts were washed with 5% potassium phosphate monobasic pH 6 buffer (2×40 mL), saturated KCl (40 mL), dried over $Na_2SO_4$, filtered, concentrated, and dried in vacuo to yield 1.8 g crude orange oil.

The crude material was purified by preparative HPLC (nine injections of ~200 mg using 2 consecutive EM Merck, RP Select B columns and eluting with 55% isocratic B:A B=95% $CH_3CN$/5% $H_2O$; A=95% $H_2O$/5% $CH_3CN$+0.04M $NH_4OAc$, pH 5.5) at a rate of 35 mL/minute, detecting at 215 nm. The desired fractions were combined and lyophilized to give 640 mg of title compound as a beige solid.

Mass Spec: (FAB); (M+$NH_4$) @ 684. (M-H) @ 665.

IR: ($CH_2Cl_2$ Film) 3144, 3052, 1823, 1584, 1487, 1447, 1246, 1215, 1065, 1028, 982, 770 $cm^{-1}$.

$^1$H-NMR: 400 MHz; $CD_3OD$: δ1.21 (m, 12H), 1.92–2.25 (m's, 4H), 2.60 (m, 2H), 3.00 (m, 2H), 3.75 (m, 1H), 4.93–5.03 (m's, 4H), 6.75 (d, 1H, J=8.1 Hz), 6.84 (s, 1H), 6.95 (d, 3H, J=7.69 Hz), 7.07 (m, 1H), 7.23 (m, 1H), 7.32 (m, 2H).

$^{13}$C-NMR: 100 MHz; $CD_3OD$: δ159.0, 158.7, 153.8, 153.7, 149.2, 145.5, 134.0, 133.8, 130.8, 130.7, 124.6, 124.6, 124.2, 120.0, 119.8, 117.3, 60.9, 59.5, 58.2, 57.3, 36.6, 31.0, 28.7, 25.7, 20.2.

Anal. Calc'd for $C_{30}H_{38}O_{13}SP \cdot NH_3 \cdot 0.89 H_2O$: C, 51.50; H, 5.73; N, 2.00; P, 4.43; S, 4.58 Found: C, 51.55; H, 5.61; N, 1.95; P, 4.22; S, 4.39.

HPLC: Rt=13.23 min (99%, UV 215); EM Lichrosphere select B (C-8, 5 m, 4×250 mm) 28–70% B:A (B=95% $CH_3CN$/5% $H_2O$+0.01M $NH_4OAc$, pH 5.5; A=95% $H_2O$/5% $CH_3CN$+0.01M $NH_4OAc$, pH 5.5), 1 mL/minute.

EXAMPLE 5

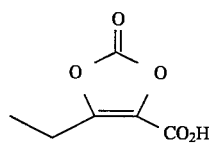

A.

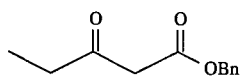

To a solution of ethyl propionyl acetate (11.10 g, 77.0 mmol) in toluene (200 mL) was added benzyl alcohol (Aldrich, 80 mL, 10 eqiv.) followed by 4-dimethylaminopyridine (Aldrich, 1.8 g, 15.4 mmol, 0.2 eq). The mixture was refluxed for 20 hours and allowed to cool to room temperature. The reaction mixture was diluted with hexane (0.5 L), washed with 5% $KHSO_4$ (2×), $H_2O$ (2×), brine, dried over $Na_2SO_4$, filtered and concentrated to give a yellow oil, which was distilled under reduced pressure to afford 11.63 g (73%) of title compound as a colorless liquid. b.p.=120° C./2 mmHg, $^1$H NMR ($CDCl_3$, 270 MHz).

B.

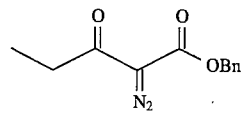

To a solution of Part A compound (11.61 g, 56.36 mmol) and Example 1 Part A sulfonyl azide, (13.55 g, 56.36 mmol) in $CH_3CN$ (420 mL) cooled to 0° C. was added triethylamine (Aldrich) (23.57 mL, 169 mmol, 3 eq) in one portion. The resultant yellow suspension was stirred at 0° C. for 10 minutes then at room temperature for 17 hours. The reaction was concentrated and triturated with 2:1 ethyl ether:petroleum ether (2×150 mL). The filtrate was concentrated and triturated again with 1:1 ethyl ether:petroleum ether (150 mL). The filtrate was concentrated and dried in vacuo affording 12.80 g of title compound as a yellow oil. $^1$H NMR ($CDCl_3$, 400 MHz), TLC: $R_f$=0.24 silica gel, 10% EtOAc in hexanes, UV and PMA detection.

C.

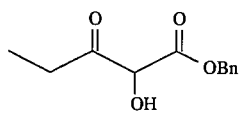

To a solution of Part B compound (12.80 g, 56.36 mmol) in 2:1 THF:water (330 mL) was added rhodium(II) acetate dimer (Aldrich, 100 mg, 0.226 mmol) in one portion. After the pale green solution was refluxed for 2 hours, additional 100 mg of rhodium(II) acetate dimer (Aldrich, 100 mg, 0.226 mmol) was added. The reaction was refluxed for two more hours, then cooled to room temperature. The reaction mixture was concentrated in vacuo and the residue extracted with EtOAc (250 mL, 150 mL, 100 mL). The combined extracts were washed with brine (3×100 mL), dried over $Na_2SO_4$, filtered, and concentrated, and dried in vacuo to give 12.58 g of title compound as a light yellow solid. $^1$H NMR ($CDCl_3$, 300 MHz), TLC: $R_f$=0.25 silica gel, 3:7 EtOAc:hexanes, UV and PMA detection.

D.

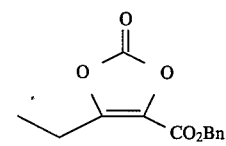

A solution of Part C compound (12.58 g, 56.36 mmol) in toluene (400 mL) cooled to 0° C. was treated with diisopropylethylamine (Aldrich, 67.8 mL, 389.2 mmol, 7 eq) followed by dropwise addition of 1.9M solution of phosgene in toluene (86.5 mL, 166.8 mmol, 3 eq) over 30 minutes. The resultant yellow suspension was stirred for 30 minutes at 0° C. and then at room temperature overnight (15 hours). The reaction mixture was diluted with EtOAc (500 mL), washed with 5% KHSO₄ (2×200 mL), water (200 mL), brine, dried over Na₂SO₄, filtered, concentrated and adsorbed onto Celite and purified on a 7×25 cm silica gel column eluting with 10% EtOAc in hexanes (5 L). Desired fractions were combined, concentrated, and dried in vacuo affording 7.395 g of title compound as an orange oil. (53% yield from Part A compound over 3 steps).

TLC: $R_f$=0.42, silica gel, 3:7 EtOAc:hexanes, UV and PMA detection.

Mass Spec: (CI); (M+NH₄) @ 266, MW=248.

$^1$H-NMR: 300 MHz; CDCl₃: δ1.25(t, 3H, J=7.5 Hz), 2.85 (q, 2H, J=7.5 Hz), 5.33(s, 2H), 7.40(m, 5H).

$^{13}$C-NMR: 75 MHz; CDCl₃: δ156.7, 153.5, 150.1, 134.5, 128.7, 128.6, 128.5, 128.4, 67.3, 18.6, 10.8.

E.

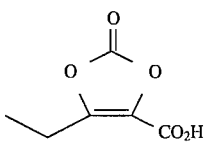

To a solution of Part D compound (7.395 g, 29.79 mmol) in EtOH (250 mL) was added Pd(OH)₂/C (Aldrich, 320 mg), and the reaction mixture was hydrogenated under a hydrogen balloon for 30 min. The reaction mixture was filtered through a plug of Celite on a Millipore filter (45 μm nylon). The filtrate was concentrated, stripped with CH₂Cl₂/toluene and dried in vacuo to yield 4.47 g of title compound as a yellow solid.

$^1$H-NMR, $^{13}$C-NMR: (300 MHz, 75 MHz; CDCl₃).

EXAMPLE 6

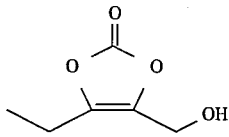

A solution of Example 5 compound (3.99 g, 25.25 mmol) in CH₂Cl₂ (85 mL) cooled to 0° C. was treated with anhydrous DMF (Aldrich Sure Seal, 300 μL) followed by dropwise addition of oxalyl chloride (Aldrich, 2.42 mL, 27.78 mmol, 1.1 eq). The reaction was stirred at 0° C. for 10 minutes then at room temperature for one hour. The reaction mixture was concentrated in vacuo, stripped with CH₂Cl₂/toluene (2×) and dried in vacuo for 30 min to give the corresponding acid chloride.

The above acid chloride was dissolved in CH₂Cl₂ (70 mL) cooled to −78° C. and treated with a solution of tetrabutylammonium borohydride (Aldrich, 7.15 g, 27.78 mmol, 1.1 eq) in CH₂Cl₂ (25 mL) over 15 minutes, stirred at −78° C. for one hour, quenched with 0.1N HCl (50 mL), allowed to warm to room temperature and concentrated in vacuo. The residue was diluted with EtOAc (300 mL) and water (50 mL) and the layers separated. The aqueous layer was saturated with NaCl and extracted with EtOAc (3×100 mL). The combined EtOAc extract was washed with brine (4×150 mL) (pH=6), dried over Na₂SO₄, filtered, and concentrated affording 3.80 g of title compound as a yellow oil. $^1$H NMR (CDCl₃, 300 MHz). TLC: $R_f$=0.40, silica gel, 8:2 EtOAc:hexanes, UV and PMA detection.

EXAMPLE 7

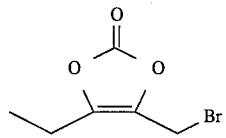

To a solution of Example 6 compound (3.80 g, 25.25 mmol) in CH₂Cl₂ (125 mL) cooled to 0° C. was added carbon tetrabromide (Aldrich, 9.95 g, 30.0 mmol, 1.2 eq) in one portion followed by triphenylphosphine (Aldrich, 7.21 g, 27.50 mmol, 1.1 eq) in one portion. The reaction was stirred at 0° C. for 30 minutes, concentrated, adsorbed onto Celite and purified on a 5×25 cm silica gel column eluting with 10% EtOAc in hexanes (3 L). The desired fractions were combined, concentrated, and dried in vacuo to afford 3.46 g (63% from Example 5 Part D compound over 4 steps) of title compound as a light brown liquid. TLC: $R_f$=0.62 silica gel, 1:1 EtOAc:hexanes, UV and PMA detection.

Mass Spec: (CI); (M+NH₄) @ 224, MW=206.

IR: (CH₂Cl₂ Film) 1825, 1723, 1308, 1227, 1196, 1115, 1063, 988, 768, 650 cm$^{-1}$.

$^1$H-NMR: 300 MHz; CDCl₃: δ1.18(t, 3H, J=7.5 Hz), 2.46(q, 2H, J=7.5 Hz), 4.19(s, 2H).

$^{13}$C-NMR: 75 MHz; CDCl₃: δ151.7, 142.5, 133.7, 18.1, 17.4, 10.8.

Anal. Calc'd for C₆H₇O₃Br: C, 34.81; H, 3.41 Found: C, 34.74; H, 3.41.

HPLC: Rt=13.5 min (75.2%, UV 215); EM Lichrosphere select B (C-8, 5μ, 4×250 mm) 28–70% B:A (B=95% CH₃CN/5%H₂O+0.01M NH₄OAc, pH 5.5; A=95% H₂O/5%CH₃CN+0.01M NH₄OAc, pH 5.5), 1 mL/minute.

EXAMPLE 8

α-[Bis[[5-ethyl-2-oxo-1,3-dioxol-4-yl]methoxy]phosphinyl]-3-phenoxybenzenebutanesulfonic acid, ammonium salt

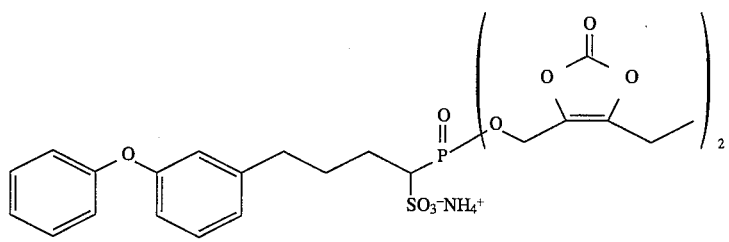

The Example 4 Part A triacid was azeotroped with EtOAc/toluene (3×) and dried in vacuo overnight to give a clear reddish oil.

To a solution of dried triacid (730 mg, 1.89 mmol) in CH₃CN (Aldrich Sure Seal, 15 mL) was added dropwise diisopropylethylamine (Fluka, 1.24 mL, 7.17 mmol, 3.8 eq) followed by dropwise addition of the Example 7 bromide (1.48 g, 7.17 mmol, 3.8 eq). The reaction was stirred for 100 hrs while monitoring the ratio of product formation versus Example 7 bromide by HPLC. The reaction was diluted with EtOAc (50 mL) and washed with 5% potassium phosphate monobasic pH 2 (3×40 mL). The combined aqueous layers were extracted with EtOAc (2×25 mL). The combined EtOAc extracts were washed with 5% potassium phosphate monobasic pH 6 buffer (2×40 mL), saturated KCl (40 mL), dried over $Na_2SO_4$, filtered, concentrated, and dried in vacuo to yield 1.58 g crude brown oil.

The crude material was purified by preparative HPLC; eight injections of ~200 mg using 2 consecutive EM Merck, RP Select B columns and eluting with 51% isocratic B:A (B=95% $CH_3CN$/5%$H_2O$; A=95% $H_2O$/5%$CH_3CN$+0.04M $NH_4OAc$, pH 5.5) at a rate of 35 mL/minute, detecting at 215 nm. The desired fractions were combined and lyophilized to give 505 mg of title compound as a beige solid.

Mass Spec: (FAB); (M+$NH_4$) @ 656. (M-H)@ 637.

IR: ($CH_2Cl_2$ Film) 3144, 3052, 1825, 1732, 1582, 1487, 1447, 1408, 1312, 1246, 1211, 1192, 1063, 1028, 1009, 988, 770 cm⁻¹.

¹H-NMR: 400 MHz; $CD_3OD$: δ1.17 (m, 6H), 1.70–2.25 (m's, 4H), 2.55 (m, 6H), 3.35 (m, 1H), 4.93 (d, 2H, J=9.0 Hz), 5.00 (dd, 2H, J=7.0, 3.0 Hz), 6.77 (dd, 1H, J=6.4, 1.7 Hz), 6.84 (s, 1H), 6.97 (d, 3H, J=7.69 Hz), 7.07 (t, 1H, J=7.4 Hz), 7.23 (t, 1H, J=7.7 Hz), 7.32 (m, 2H).

¹³C-NMR: 100 MHz; $CD_3OD$: δ159.0, 158.7, 153.9, 153.8, 146.3, 145.5, 134.9, 134.8, 134.7, 134.6, 133.9, 130.8, 130.8, 130.7, 124.6, 124.6, 124.2, 120.0, 119.8, 117.3, 60.8, 59.5, 58.1, 58.0, 57.1, 36.5, 30.9, 28.7, 18.1, 11.5.

Anal. Calc'd for $C_{28}H_{31}O_{13}SP \cdot NH_3 \cdot 0.37H_2O$: C, 50.78; H, 5.29; N, 2.11; P, 4.68; S, 4.84 Found: C, 50.65; H, 5.35; N, 2.24; P, 4.84; S, 4.73.

HPLC: Rt=11.89 min (99%, UV 215); EM Lichrosphere select B (C-8, 5μ, 4×250 mm) 28–70% B:A (B=95% $CH_3CN$/5%$H_2O$+0.01M $NH_4OAc$, pH 5.5; A=95% $H_2O$/5%$CH_3CN$+0.01M $NH_4OAc$, pH 5.5), 1 mL/minute.

EXAMPLE 9

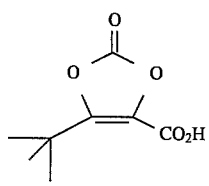

A.

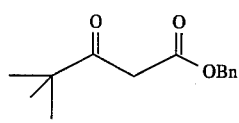

To a solution of methyl 4,4-dimethyl-3-oxo-pentanoate (11.98 mL, 75 mmol) in toluene (200 mL) was added benzyl alcohol (Aldrich, 80 mL, 10.3 eq) followed by 4-dimethylaminopyridine (Aldrich, 1.37 g, 11.25 mmol, 0.15 eq). The mixture was refluxed for 44 hours and allowed to cool to room temperature. The reaction mixture was diluted with hexane (0.3 L), washed with 5% $KHSO_4$ (2×200 mL), $H_2O$ (2×200 mL), brine, dried over $Na_2SO_4$, filtered and concentrated to give a yellow oil, which was distilled under reduced pressure to afford 10.75 g (61%) of title compound. b.p.= 128°–130° C./2 mm; ¹H NMR and ¹³C NMR ($CDCl_3$, 300 MHz, 75 MHz).

B.

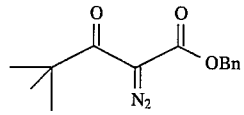

To a solution of Part A compound (10.75 g, 45.88 mmol) and Example 1 Part A sulfonyl azide, (11.02 g, 45.88 mmol) in $CH_3CN$ (400 mL) cooled to was added distilled triethylamine (19.10 mL, 137.64 mmol, 3 eq) in one portion. The resultant yellow suspension was stirred at 0° C. for 30 minutes then at room temperature overnight. The reaction was concentrated and triturated with 2:1 ethyl ether:petroleum ether (2×250 mL). The filtrate was concentrated and triturated again with 1:1 ethyl ether:petroleum ether (200 mL). The filtrate was concentrated and dried in vacuo affording 12.89 g of title compound as a yellow oil. ¹H NMR and ¹³C NMR ($CDCl_3$, 300 MHz, 75 MHz), TLC: $R_f$=0.43 silica gel, 10% EtOAc in hexanes, UV and PMA detection.

C.

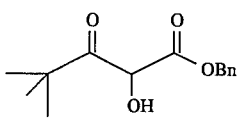

To a solution of Part B compound (45.9 mmol) in 2:1 THF:water (300 mL) was added rhodium(II) acetate dimer (Aldrich, 400 mg, 0.9 mmol) in three portions (3×100 mg every 2 hrs) and the pale green solution was refluxed overnight. The reaction mixture was concentrated in vacuo and the residue extracted with EtOAc (2×250 mL). The combined extracts was washed with brine (2×100 mL), dried over $Na_2SO_4$, filtered, concentrated, and dried in vacuo to give 12.21 g of title compound as a pale green oil. ¹H NMR and ¹³C NMR ($CDCl_3$, 300 MHz, 75 MHz), TLC: $R_f$=0.43 silica gel, 3:7 EtOAc:hexanes, UV and PMA detection.

D.

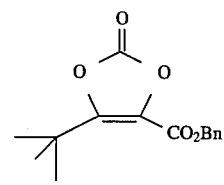

A solution of Part C compound (44 mmol) in toluene (250 mL) cooled to 0° C. was treated with diisopropylethylamine (Aldrich, 53.2 mL, 308.7 mmol, 7 eq) followed by the dropwise addition of a 1.9M solution of phosgene in toluene (68.3 mL, 132 mmol, 3 eq) over 20 minutes. The resultant solution was stirred for 30 minutes at 0° C. and then at room temperature overnight. The reaction mixture was diluted with EtOAc (300 mL), washed with 5% $KHSO_4$ (2×200 mL), water (200 mL), brine, dried over Na$_2$SO$_4$, filtered, concentrated and adsorbed onto Celite and purified on a 10×25 cm silica gel column eluting with 10% EtOAc in hexanes (4 L). The desired fractions were combined, concentrated, and dried in vacuo affording 9.10 g of title compound which was recrystallized from hot hexane. White crystals were collected by filtration and dried in vacuo to give 5.36 g (75% from Part A compound) of title compound. TLC: R$_f$=0.57 silica gel, 3:7 EtOAc:hexanes, UV and PMA detection.

Mass Spec: (CI); (M+NH$_4$) @ 294.

m.p.=68°–70° C.

IR: (KBr) 3434, 2972, 1836, 1732, 1663, 1341, 1142, 964, 758, cm$^{-1}$.

$^1$H-NMR: 300 MHz; CDCl$_3$: δ1.38 (s, 9H), 5.31 (s, 2H), 7.40 (m, 5H).

$^{13}$C-NMR: 75 MHz; CDCl$_3$: δ157.2, 151.0, 135.2, 129.4, 129.2, 68.2, 33.5, 28.4.

Anal. Calc'd for C$_{15}$H$_{16}$O$_5$: C, 65.20; H, 5.84 Found: C, 65.20; H, 5.86.

E.

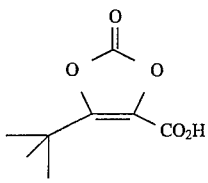

To a solution of Part D compound (9.70 g, 35 mmol) in EtOH (250 mL) was added Pd(OH)$_2$/C (Aldrich, 430 mg). The reaction mixture was hydrogenated under a hydrogen balloon for 30 minutes. The reaction mixture was filtered through a plug of Celite on a Millipore filter (45 μm nylon). The filtrate was concentrated, stripped with CH$_2$Cl$_2$ and dried in vacuo to yield 6.78 g of title compound as a yellow green solid. $^1$H NMR and $^{13}$C NMR(CDCl$_3$, 300, 75 MHz). A sample was crystallized from hexane/EtOAc as a white crystalline compound.

Mass Spec: (CI); (M+NH$_4$) @ 204. m.p.=137°–139° C.

IR: (KBr) 3435, 2978, 1832, 1697, 1645, 1445, 1159, 1123, 762 cm$^{-1}$.

$^1$H-NMR: 300 MHz; CDCl$_3$: δ1.42 (s, 9H,) 7.27 (bs, 1H).

$^{13}$C-NMR: 75 MHz; CDCl$_3$: δ161.1, 149.3, 128.1, 33.0, 27.60.

Anal. Calc'd for C$_8$H$_{10}$O$_5$: C, 51.61; H, 5.41 Found: C, 51.69; H, 5.02.

EXAMPLE 10

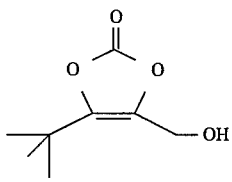

A solution of Example 9 compound (6.17 g, 33.13 mmol) in CH$_2$Cl$_2$ (150 mL) cooled to 0° C. was treated with anhydrous DMF (Aldrich Sure Seal, 350 μL) followed by dropwise addition of oxalyl chloride (Aldrich, 3.18 mL, 36.44 mmol, 1.1 eq). The reaction was stirred at 0° C. for 20 minutes then at room temperature for one hour. The reaction mixture was concentrated in vacuo, stripped from CH$_2$Cl$_2$/toluene (2×) and dried in vacuo for one hour to give acid chloride.

The above acid chloride (~33 mmol) was dissolved in CH$_2$Cl$_2$ (150 mL) cooled to −78° C. and treated with a solution of tetrabutylammonium borohydride (Aldrich, 9.38 g, 36.44 mmol, 1.1 eq) in CH$_2$Cl$_2$ (50 mL) over 25 minutes. The reaction mixture was stirred at −78° C. for one hour and quenched with 0.1N HCl (100 mL). The reaction was allowed to warm to room temperature and concentrated in vacuo. The residue was diluted with EtOAc (100 mL) and water (50 mL) and the layers were separated. The aqueous layer was saturated with NaCl and extracted with EtOAc (2×100 mL). The combined EtOAc extracts were washed with brine (200 mL), dried over Na$_2$SO$_4$, filtered, and concentrated affording 10.2 g crude orange oil. The residue was purified on a 7×20 cm silica gel column eluting with 1:1 EtOAc:hexanes (2 L). The desired fractions were combined, concentrated, and dried in vacuo to afford 3.98 g (72% from Example 9 Part D compound) of title compound as a yellow oil. $^1$H NMR and $^{13}$C NMR(CDCl$_3$, 300, 75 MHz). TLC: R$_f$=0.34 silica gel, 1:1 EtOAc:hexanes, UV and PMA detection.

EXAMPLE 11

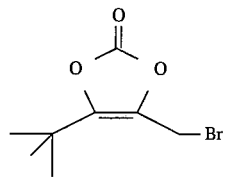

To a solution of Example 10 compound (3.76 g, 21.85 mmol) in CH$_2$Cl$_2$ (125 mL) cooled to 0° C. was added carbon tetrabromide (Aldrich, 8.70 g, 26.22 mmol, 1.2 eq) in one portion followed by triphenylphosphine (Aldrich, 6.30 g, 24.04 mmol, 1.1 eq) in one portion. The reaction was stirred at 0° C. for 35 minutes, concentrated, adsorbed onto Celite and purified on a 5×25 cm silica gel column eluting with 10% EtOAc in hexanes (3 L). The desired fractions were combined, concentrated, and dried in vacuo to afford 4.30 g (84%) of title compound as a yellow liquid. TLC: R$_f$=0.47 silica gel, 3:7 EtOAc:hexanes, UV and PMA detection.

Mass Spec: (CI); (M+NH$_4$) @ 252.

IR: (CH$_2$Cl$_2$ Film) 2965, 1832, 1319, 1271, 1188, 1105, 968, 770, 652 cm$^{-1}$.

$^1$H-NMR: 270 MHz; CDCl$_3$: δ1.32 (s, 9H,), 4.31 (s, 2H).

$^{13}$C-NMR: 68 MHz; CDCl$_3$: δ151.3, 148.0, 132.9, 32.2, 27.6, 19.5.

Anal. Calc'd for C$_8$H$_{11}$O$_3$Br: C, 40.77; H, 4.73; Br, 33.90 Found: C, 40.77; H, 4.32; Br, 33.72.

HPLC: Rt=17.5 min (97%, UV 215); EM Lichrosphere select B (C-8, 5μ, 4×250 mm) 28–70% B:A (B=95% CH$_3$CN/5%H$_2$O+0.01M NH$_4$OAc, pH 5.5; A=95% H$_2$O/5%CH$_3$CN+0.01M NH$_4$OAc, pH 5.5), 1 mL/minute.

EXAMPLE 12

α-[Bis[[5-(1,1-dimethylethyl)-2-oxo-1,3-dioxol-4-yl]methoxy]phosphinyl]-3-phenoxybenzenebutanesulfonic acid, ammonium salt

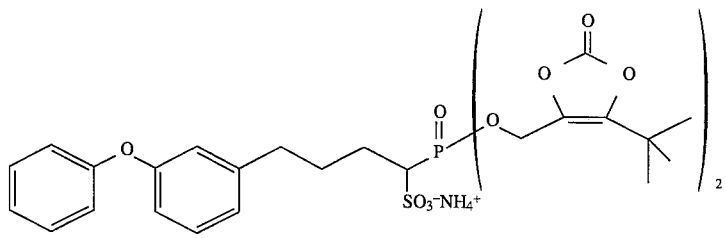

The Example 4 Part A triacid was azeotroped with EtOAc/toluene (3×) and dried in vacuo for one hour to give a clear reddish oil.

To a solution of dried triacid (804 mg, 2.08 mmol) in $CH_3CN$ (Aldrich Sure Seal, 16 mL) was added dropwise diisopropylethylamine (Fluka, 1.37 mL, 7.90 mmol, 3.8 eqiv) followed by dropwise addition of the Example 11 bromide (1.86 g, 7.90 mmol, 3.8 eq). The reaction was stirred for six days, while monitoring the ratio of product formation versus Example 11 bromide by HPLC. The reaction was concentrated in vacuo, diluted with EtOAc (100 mL) and washed with 5% potassium phosphate monobasic pH 2 buffer (3×40 mL). The combined aqueous layers were extracted with EtOAc (2×25 mL). The combined EtOAc extracts were washed with 5% potassium phosphate monobasic pH 6 buffer (2×40 mL), brine (40 mL), dried over $Na_2SO_4$, filtered, concentrated, and dried in vacuo to yield 2.2 g crude orange oil.

The crude material was purified by preparative HPLC; eleven injections of ~200 mg using 2 consecutive EM Merck, RP select B columns and eluting with 58% isocratic B:A (B=95% $CH_3CN$/5% $H_2O$; A-95% $H_2O$/5% $CH_3CN$+ 0.04M $NH_4OAc$, pH 5.5) at a rate of 35 mL/minute, detecting at 215 nM. The desired fractions were combined and lypholized to give 916 mg (62%) of title compound as a beige solid.

Mass Spec: (electrospray); (M+H) @ 695.

IR: ($CH_2Cl_2$ Film) 3480, 2974, 1829, 1584, 1487, 1248, 1119, 1026, 982, 770 $cm^{-1}$.

$^1$H-NMR: 400 MHz; $CD_3OD$: δ1.28 (2s, 18H), 1.93–2.21 (m's, 4H), 2.60 (m, 2H), 3.31–3.45 (m's, 2H), 4.98–5.11 (m's, 4H), 6.75 (m, 1H,), 6.84 (s, 1H), 6.95 (d, 3H, J=8.55 Hz), 7.07 (m, 1H), 7.21 (m, 1H), 7.33 (m, 2H).

$^{13}$C-NMR: 100 MHz; $CD_3OD$: δ158.7, 158.5, 153.2, 153.1, 151.2, 151.1, 145.3, 133.9, 133.7, 130.6, 124.4, 124.0, 119.9, 119.6, 117.2, 60.7, 59.3, 59.0, 58.2, 36.4, 32.9, 30.8, 28.6, 28.1.

Anal. Calc'd for $C_{32}H_{39}O_{13}SP \cdot NH_3 \cdot 0.56 H_2O$: C, 53.25; H, 6.02; N, 1.94; P, 4.26; S, 4.30 Found: C, 53.24; H, 6.35; N, 1.84; P, 4.26; S, 4.31.

HPLC: Rt=13.04 min (99%, UV 215); EM Lichrosphere select B (C-8, 5μ, 4×250 mm) 28–70% B:A (B=95% $CH_3CN$/5% $H_2O$+0.01M $NH_4OAc$, pH 5.5; A=95% $H_2O$/ 5% $CH_3CN$+0.01M $NH_4OAc$, pH 5.5), 1 mL/minute.

EXAMPLE 13

A.

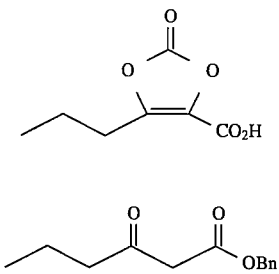

To a solution of ethyl butyryl acetate (11.87 g, 75.0 mmol) in toluene (180 mL) was added benzyl alcohol (Aldrich, 72 mL, 10 eqiv.) followed by 4-dimethylaminopyridine (Aldrich, 1.7 g, 15.0 mmol, 0.2 eq). The mixture was refluxed for 20 hours and allowed to cool to room temperature. The reaction mixture was diluted with hexane (0.5 L), washed with 5% aqueous $KHSO_4$ (2×'s), $H_2O$ (2×'s), brine, dried over $Na_2SO_4$, filtered and concentrated to give a yellow oil, which was distilled under reduced pressure to afford 10.40 g (63%) of title compound as a colorless liquid. b.p.=127° C./1.5 mmHg; $^1$H NMR ($CDCl_3$, 270 MHz).

B.

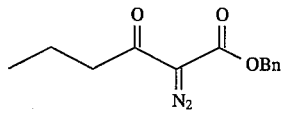

To a solution of Part A compound (10.40 g, 47.27 mmol) and Example 1 Part A sulfonyl azide, (11.36 g, 47.27 mmol) in $CH_3CN$ (400 mL) cooled to 0° C. was added triethylamine (Aldrich) (19.80 mL, 142 mmol, 3 eq) in one portion. The resultant yellow suspension was stirred at 0° C. for 10 minutes then at room temperature for 22 hours. The reaction was concentrated and triturated with 2:1 ethyl ether:petroleum ether (2×150 mL). The filtrate was concentrated and triturated again with 1:1 ethyl ether:petroleum ether (150 mL). The filtrate was concentrated and dried in vacuo affording 11.695 g (100%) of title compound as a yellow oil. A sample was crystallized from petroleum ether as a yellow crystalline compound.

TLC: $R_f$=0.34, silica gel, 1:9 EtOAc:hexanes, UV and PMA detection. m.p. 29°–30° C.

$^1$H-NMR: 400 MHz; $CDCl_3$: δ0.95 (t, 3H, J=7.5 Hz), 1.67 (m, 2H), 2.82 (t, 2H, J=7.5 Hz), 5.26 (s, 2H), 7.37 (m, 5H).

$^{13}$C-NMR: 67.8 MHz; CDCl$_3$: δ192.6, 161.2, 135.1, 128.6, 128.5, 128.3, 66.8, 42.1, 17.7, 13.6.

IR: (KBr pellet) 3437, 2965, 2135, 1719, 1657, 1388, 1300, 1213, 1138, 1094, 1017, 746, 698 cm$^{-1}$ Mass Spec: (CI); (M+H) @ 247, MW=246.

Anal Calc'd for C$_{13}$H$_{14}$N$_2$O$_3$: C, 63.40; H, 5.73; N, 11.38 Found: C, 63.26; H, 5.61; N, 11.66.

C.

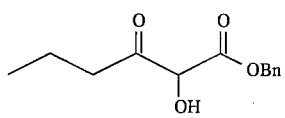

To a solution of Part B compound (11.30 g, 45.89 mmol) in 2:1 THF:water (300 mL) was added rhodium(II) acetate dimer (Aldrich, 120 mg, 0.271 mmol) in one portion. The pale green solution was refluxed for 2 hours and the reaction was allowed to cool to room temperature. The reaction mixture was concentrated in vacuo and the residue extracted with EtOAc (200 mL, 2×100 mL). The combined extract was washed with brine (2×100 mL), dried over Na$_2$SO$_4$, filtered, and concentrated, and dried in vacuo to give 10.85 g (100%) of crude title compound. A sample was crystallized from petroleum ether and EtOAc as a white flaky compound.

TLC: R$_f$=0.34, silica gel, 3:7 EtOAc:hexanes, UV and PMA detection.

m.p. 30°–31° C.

$^1$H-NMR: 300 MHz; CDCl$_3$: δ0.85 (t, 3H, J=7.5 Hz), 1.60 (m, 2H), 2.59 (m, 2H), 3.93 (d, 1H, J=7.0 Hz), 4.81 (d, 1H, J=7.0 Hz), 5.25 (q, 2H, J=12.0, 5.0 Hz), 7.37 (m, 5H).

$^{13}$C-NMR: 75 MHz; CDCl$_3$: δ204.0, 168.1, 134.6, 128.7, 128.6, 128.5, 128.4, 77.8, 67.9, 40.5, 16.7, 13.4.

IR: (KBr pellet) 3435, 2965, 1751, 1723, 1634, 1456, 1379, 1265, 1215, 1132, 752, 698 cm$^{-1}$.

Mass Spec: (CI); (M+NH$_4$) @ 254, MW=236.

Anal. Calc'd for C$_{13}$H$_{16}$O$_4$: C, 65.89; H, 6.84 Found: C, 65.89; H, 6.91.

D.

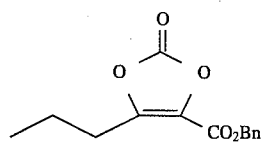

A solution of Part C compound (10.70 g, 45.34 mmol) in toluene (300 mL) cooled to 0° C. was treated with diisopropylethylamine (Aldrich, 55.0 mL, 317.4 mmol, 7 eq) followed by dropwise addition of a 1.9M solution of phosgene in toluene (71 mL, 136 mmol, 3 eq) over 20 minutes. The resultant yellow suspension was stirred for 30 minutes at 0° C. and then at room temperature overnight (15 hours). The reaction mixture was diluted with EtOAc (400 mL), washed with 5% aqueous KHSO$_4$ (2×200 mL), water (200 mL), brine, dried over Na$_2$SO$_4$, filtered, concentrated, adsorbed onto Celite, and purified on a 7×25 cm silica gel column eluting with 10% EtOAc in hexanes (5 L). The desired fractions were combined, concentrated, and dried in vacuo affording 5.877 g of title compound as a yellow oil. (50% yield from Part A compound over 3 steps).

TLC: R$_f$=0.44, silica gel, 3:7 EtOAc:hexanes, UV and PMA detection.

$^1$H-NMR: 400 MHz; CDCl$_3$: δ0.96 (t, 3H, J=7.5 Hz), 1.68 (m, 2H), 2.77 (t, 2H, J=7.5 Hz), 5.31 (s, 2H), 7.40 (m, 5H).

$^{13}$C-NMR: 100 MHz; CDCl$_3$: δ156.7, 152.6, 150.1, 134.5, 129.6, 128.7, 128.5, 67.4, 26.7, 19.9, 13.3.

E.

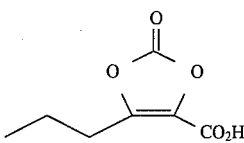

To a solution of Part D compound (5.5 g, 21.0 mmol) in EtOH (200 mL) was added Pd(OH)$_2$/C (Aldrich, 275 mg), and the reaction was hydrogenated under a hydrogen balloon for 30 min. The reaction mixture was filtered through a plug of Celite on a Millipore filter (45 µm nylon). The filtrate was concentrated, stripped with CH$_2$Cl$_2$/toluene and dried in vacuo to yield 3.627 g (100%) of title compound as a light yellow solid. A sample of pure title acid was crystallized from hexane and EtOAc.

m.p. 87°–88° C.

$^1$H-NMR: 400 MHz; CDCl$_3$: δ1.02 (t, 3H, J=7.5 Hz), 1.73 (m, 2H), 2.84 (t, 2H, J=7.5 Hz), 11.4 (bs, 1H).

$^{13}$C-NMR:100 MHz; CDCl$_3$: δ161.4, 154.9, 149.8, 128.9, 26.9, 20.0, 13.4.

IR: (KBr pellet) 2969, 1832, 1717, 1703, 1669, 1462, 1192, 1159, 957, 756 cm$^{-1}$.

Mass Spec: (CI); (M+NH$_4$) @190, (M-H) @ 171, MW=172.

Anal. Calc'd for C$_7$H$_8$O$_5$: C, 48.84; H, 4.68 Found: C, 48.97; H, 4.65.

EXAMPLE 14

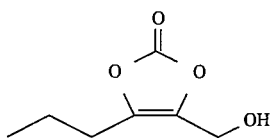

To a solution of Example 13 compound (3.50 g, 20.35 mmol) in CH$_2$Cl$_2$ (60 mL) cooled to 0° C. was added anhydrous DMF (Aldrich Sure Seal, 200 µL) followed by dropwise addition of oxalyl chloride (Aldrich, 1.95 mL, 22.38 mmol, 1.1 eq). The reaction was stirred at 0° C. for 15 minutes then at room temperature for one hour. The reaction mixture was concentrated in vacuo, stripped with CH$_2$Cl$_2$/toluene (2×) and dried in vacuo for 30 min to give acid chloride.

The above acid chloride was dissolved in CH$_2$Cl$_2$ (40 mL) cooled to −78° C. and treated with a solution of tetrabutylammonium borohydride (Aldrich, 5.76 g, 22.38 mmol, 1.1 eq) in CH$_2$Cl$_2$ (20 mL) over 15 minutes, stirred at −78° C. for one hour and quenched with 0.1N HCl (40 mL). The reaction mixture was allowed to warm to room temperature and concentrated in vacuo. The residue was diluted with EtOAc (300 mL) and water (50 mL) and the layers were separated. The aqueous layer was saturated with NaCl and extracted with EtOAc (2×100 mL). The combined EtOAC extracts was washed with brine (2×), dried over Na$_2$SO$_4$, filtered, and concentrated in vacuo. The crude product (yellow oil) was flash-chromatographed (eluting with 50% EtOAc/hexane) to afford 1.968 g (61% from Example 13 Part D compound over 3 steps) of pure title compound as a light yellow liquid.

TLC: $R_f$=0.47, silica gel, 8:2 EtOAc:hexanes, UV and PMA detection.

$^1$H-NMR: 400 MHz; CDCl$_3$: δ0.97 (t, 3H, J=7.5 Hz), 1.65 (m, 2H), 1.95 (bs, 1H), 2.43 (t, 2H, J=7.5 Hz), 4.42 (d, 2H, J=6.4 Hz).

$^{13}$C-NMR:100 MHz; CDCl$_3$: δ153.0, 140.9, 137.4, 52.7, 25.1, 19.8, 13.0.

IR: (CH$_2$Cl$_2$ film) 3432, 2967, 1817, 1730, 1320, 1248, 1177, 1028, 1003, 774 cm$^{-1}$.

Mass Spec: (CI); (M+NH$_4$) @176, MW=158.

Anal. Calc'd for C$_7$H$_{10}$O$_4$•0.03 H$_2$O: C, 53.00; H, 6.39 Found: C, 53.44; H, 6.83.

EXAMPLE 16

α-[Bis[[2-oxo-5-propyl-1,3-dioxol-4-yl]methoxy]phosphinyl]-3-phenoxybenzenebutanesulfonic acid, ammonium salt

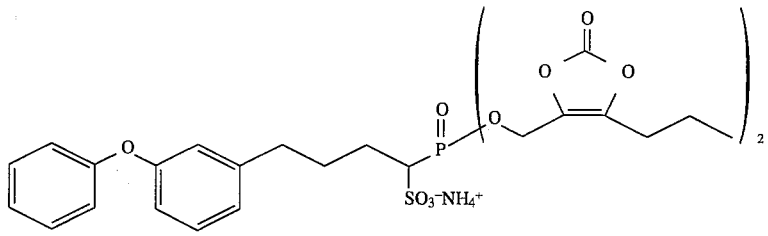

EXAMPLE 15

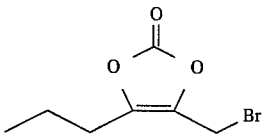

To a solution of Example 14 compound (1.90 g, 12.03 mmol) in CH$_2$Cl$_2$ (50 mL) cooled to 0° C. was added carbon tetrabromide (Aldrich, 4.787 g, 14.43 mmol, 1.2 eq) in one portion followed by triphenylphosphine (Aldrich, 3.47 g, 13.23 mmol, 1.1 eq) in one portion. The reaction was stirred at 0° C. for one hour, concentrated, adsorbed onto Celite and purified on a 5×25 cm silica gel column eluting with 10% EtOAc in hexanes (3 L). The desired fractions were combined, concentrated, and dried in vacuo to afford 2.30 g (87%) of title compound as a colorless liquid.

TLC: $R_f$=0.64, silica gel, 1:1 EtOAc:hexanes, UV and PMA detection.

Mass Spec: (CI); (M+NH$_4$) @ 238, MW=220.

IR: (CH$_2$Cl$_2$ film) 2967, 1832, 1721, 1464, 1433, 1308, 1227, 1190, 1115, 1088, 968, 770, 644 cm$^{-1}$.

$^1$H-NMR: 400 MHz; CDCl$_3$: δ1.00 (t, 3H, J=7.5 Hz), 1.67 (m, 2H), 2.45 (t, 2H, J=7.5 Hz), 4.25 (s, 2H).

$^{13}$C-NMR: 100 MHz; CDCl$_3$: δ151.8, 141.5, 134.7, 25.7, 19.8, 18.2, 13.4.

Anal. Calc'd for C$_7$H$_9$O$_3$Br: C, 38.04; H, 4.10; Br, 36.15 Found: C, 38.52; H, 3.98; Br, 36.59.

HPLC: Rt=15.25 min (97.3%, UV 215); EM Lichrosphere select B (C-8, 5µ, 4×250 mm) 28–70% B:A (B=95% CH$_3$CN/5%H$_2$O+0.01M NH$_4$OAc, pH 5.5; A=95% H$_2$O/ 5%CH$_3$CN+0.01M NH$_4$OAc, pH 5.5), 1 mL/minute.

The Example 4 Part A triacid was azeotroped with EtOAc/ toluene (3×'s) and dried in vacuo overnight to give a clear reddish oil.

To a solution of dried triacid (730 mg, 1.89 mmol) in CH$_3$CN (Aldrich Sure Seal, 15 mL) was added dropwise diisopropylethylamine (Fluka, 1.24 mL, 7.17 mmol, 3.8 eq) followed by dropwise addition of the Example 15 bromide (1.59 g, 7.17 mmol, 3.8 eq). The reaction was stirred for 7 days, while monitoring the ratio of product formation versus Example 15 bromide by HPLC. The reaction mixture was concentrated in vacuo. The residue was diluted with EtOAc (100 mL) and washed with 5% potassium phosphate monobasic pH 2 buffer (3×40 mL) and the combined aqueous layers were extracted with EtOAc (2×40 mL). The combined EtOAc extracts were washed with 5% potassium phosphate monobasic pH 6 buffer (2×40 mL), saturated KCl (40 mL), dried over Na$_2$SO$_4$, filtered, concentrated, and dried in vacuo to yield 1.837 g of a crude brown oil.

The crude material was purified by preparative HPLC. Nine injections of ~200 mg using 2 consecutive EM Merck, RP Select B column and eluting with 57% isocratic B:A (B=95% CH$_3$CN/5%H$_2$O; A=95% H$_2$O/5%CH$_3$CN+0.04M NH$_4$OAc, pH 5.5) at a rate of 35 mL/minute, detecting at 215 nm. The desired fractions were combined and lyophilized to give 743 mg of title compound as a beige solid.

Mass Spec: (electrospray); (M+Na) @ 705, MW=683.

IR: (CH$_2$Cl$_2$ Film) 3144, 3050, 2967, 1827, 1732, 1584, 1487, 1447, 1406, 1310, 1244, 1192, 1059, 1028, 982, 770 cm$^{-1}$.

$^1$H-NMR: 400 MHz; CD$_3$OD: δ0.94 (m, 6H), 1.59 (m, 4H), 1.85–2.23 (m's, 4H), 2.50 (m, 4H), 2.62 (m, 2H), 3.35 (m, 1H), 4.93 (d, 2H, J=9.0 Hz), 5.00 (dd, 2H, J=7.0, 3.0 Hz), 6.77 (dd, 1H, J=6.4, 1.7 Hz), 6.84 (s, 1H), 6.97 (d, 3H, J=7.69 Hz), 7.07 (t, 1H, J=7.4 Hz), 7.23 (t, 1H, J=7.7 Hz), 7.32 (m, 2H).

$^{13}$C-NMR: 100 MHz; CD$_3$OD: δ159.0, 158.7, 153.9, 153.8, 145.5, 145.1, 135.6, 135.4, 130.8, 130.7, 124.6, 124.2, 120.0, 119.8, 117.3, 60.9, 59.5, 58.0, 57.1, 36.6, 31.0, 28.7, 26.2, 21.0, 13.6.

Anal. Calc'd for $C_{30}H_{35}O_{13}SP \cdot NH_3 \cdot 0.33\ H_2O$: C, 52.25; H, 5.65; N, 2.03; P, 4.49; S, 4.65 Found: C, 51.90; H, 5.57; N, 2.38; P, 4.80; S, 4.62.

HPLC: Rt=12.27 min (99%, UV 215); EM Lichrosphere select B (C-8, 5μ, 4×250 mm) 28–70% B:A (B=95% $CH_3CN$/5% $H_2O$+0.01M $NH_4OAc$, pH 5.5; A=95% $H_2O$/5%$CH_3CN$+0.01M $NH_4OAc$, pH 5.5), 1 mL/minute.

EXAMPLE 17

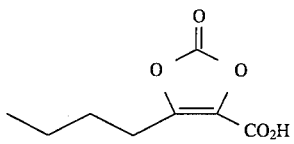

A.

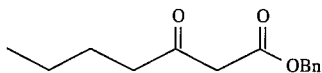

A solution of ethyl pentyryl acetate (12.33 g, 71.6 mmol), benzyl alcohol (74 mL), and 4-dimethylaminopyridine (1.16 gm) in toluene (200 mL) was refluxed for 21 hours. Work-up and distillation afforded title compound: 77% yield; bp 145°–148° C. @ 2.0 mm Hg; TLC $R_f$ 0.50 (3:7-EtOAc:hexanes); $^1$H-NMR (CDCl$_3$) δ0.88 (t, 3H, J=7.3 Hz), 1.28 (m, 2H), 1.56 (m, 2H), 2.51 (t, 2H, J=7.0 Hz), 3.48 (s, 2H), 5.18 (s, 2H), 7.36 (s, 5H); $^{13}$C-NMR (CDCl$_3$) δ202.60, 167.03, 135.31, 128.55, 128.39, 128.34, 67.04, 49.19, 42.72, 25.47, 22.07, 13.72; IR (CH$_2$Cl$_2$ film) 2936, 1744, 1717 cm$^{-1}$; Anal. Calcd for $C_{14}H_{18}O_3$: C, 71.77; H, 7.74. Found C, 72.25; H, 7.79.

B.

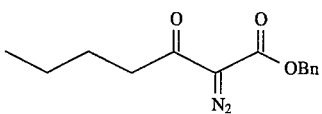

A solution of Part A compound (12.01 g, 51.3 mmol) and the Example 1 Part A sulfonylazide (12.32 g) in CH$_3$CN (400 mL) at 0° C. was treated with triethylamine (TEA) (21.4 mL). After 30 minutes at 0° C. and 4 hours at room temperature, the mixture was worked-up and flash chromatographed (Merck SiO2, 15/85-EtOAc/hexane as eluant) to provide pure title compound (12.79 g): 96% yield; TLC $R_f$ 0.52 (2:8-EtOAc:hexanes); $^1$H-NMR (CDCl$_3$) δ0.91 (t, 3H, J=7.3 Hz), 1.34 (m, 2H), 1.62 (m, 2H), 2.85 (pseudo t, 2H), 5.26 (s, 2H), 7.37 (s, 5H); $^{13}$C-NMR (CDCl$_3$) δ193.28, 161.67, 135.61, 129.13, 129.07, 128.75, 67.30, 40.43, 26.84, 22.72, 14.23; IR (CH$_2$Cl$_2$ film) 2959, 2135, 1719, 1657, 1300 cm$^{-1}$; Anal. Calcd for $C_{14}H_{16}N_2O_3$: C, 64.60; H, 6.20; N, 10.76. Found C, 64.70; H, 6.10; N, 11.02.

C.

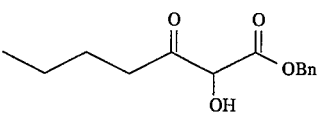

A solution of the Part B diazo compound (12.686 g, 48.7 mmol) in THF (250 mL) and H$_2$O (120 mL) was refluxed with Rh(OAc)$_2$ (165 mg) for 5 hours. Work-up provided crude title compound (12.04 g) as a yellow oil: TLC $R_f$ 0.38 (3:7-EtOAc:hexanes); $^1$H-NMR (CDCl$_3$) δ0.84 (t, 3H, J=7.3 Hz), 1.21 (m, 2H), 1.52 (m, 2H), 2.53 (m, 2H), 4.81 (s, 1H), 5.24 (m, 2H), 7.36 (s, 5H); $^{13}$C-NMR (CDCl$_3$) δ204.08, 168.06, 134.57, 128.69, 128.61, 128.49, 77.72, 67.87, 38.33, 25.26, 21.94, 13.56; IR (CH$_2$Cl$_2$ film) 3461, 2959, 1751, 1723, 1262, 1130 cm$^{-1}$; Anal. Calcd for $C_{14}H_{18}O_4$108 0.5H$_2$O: C, 64.83; H, 7.39. Found C, 64.84; H, 7.11.

D.

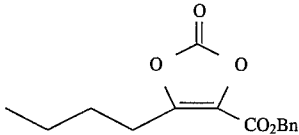

A 0° C. solution of the Part C alcohol (11.76 g, 46.9 mmol) in dry THF (230 mL) was treated with 1,1'-carbonyldiimidazole (CDI) (15.3 g) followed by diisopropylethylamine (DIPEA) (336 uL). After 5 hours the cooling bath was removed and the mixture was stirred at room temperature overnight. Work-up and flash chromatography (Merck SiO2, 15/85-EtOAc/hexane as eluant) provided pure title compound (9.99 g): 77% yield from Part B compound; TLC $R_f$ 0.34 (15:85-EtOAc:hexanes); $^1$H-NMR (CDCl$_3$) δ0.90 (t, 3H, J=7.3 Hz), 1.35 (m, 2H), 1.60 (m, 2H), 2.80 (t, 2H, J=7.6 Hz), 5.13 (s, 2H), 7.39 (s, 5H); $^{13}$C-NMR (CDCl$_3$) δ156.80, 152.85, 150.05, 134.54, 129.41, 128.84, 128.79, 128.55, 67.47, 28.45, 24.59, 21.97, 13.48; IR (CH$_2$Cl$_2$ film) 2961, 1834, 1738, 1192, 1134, 756 cm$^{-1}$; Anal. Calcd for $C_{15}H_{16}O_5$: C, 65.21; H, 5.84. Found C, 65.30; H, 6.07.

E.

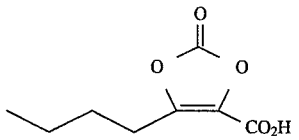

A solution of Part D compound (9.98 g, 36.1 mmol) was stirred with Pd(OH)$_2$ on carbon (20%, 490 mg) in absolute EtOH (230 mL) under an atmosphere of hydrogen (balloon) for 70 minutes. Filtration and removal of the solvent provided title compound (6.56 g) as an off-white solid): 98% yield; mp 59°–61° C.; $^1$H-NMR (CDCl$_3$) δ0.96 (t, 3H, J=7.3 Hz), 1.41 (m, 2H), 1.68 (m, 2H), 2.86 (t, 2H, J=7.5 Hz); $^{13}$C-NMR (CDCl$_3$) δ162.14, 155.54, 150.36, 129.29, 28.90, 25.28, 22.49, 13.97; IR (KBr) 3435, 2961, 1834, 1821, 1730, 1719, 1190, 1154 cm$^{-1}$; Anal. Calcd for $C_8H_{10}O_5$: C, 51.61; H, 5.41. Found C, 51.61; H, 5.73.

EXAMPLE 18

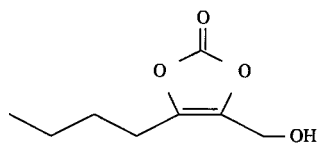

Example 17 acid (6.468 g, 34.7 mmol) was converted to title alcohol (4.254 g) in 69% yield: TLC $R_f$ 0.17 (3:7-EtOAc:hexanes); $^1$H-NMR (CDCl$_3$) δ0.94 (t, 3H, J=7.5 Hz), 1.37 (m, 2H), 1.59 (m, 2H), 2.38 (t, 1H, J=6.2 Hz), 2.45 (t, 2H, J=7.5 Hz), 4.41 (d, 2H, J=6.0 Hz); $^{13}$C-NMR (CDCl$_3$)

δ152.94, 141.31, 137.12, 53.38, 28.77, 23.47, 22.04, 13.65; IR (CH$_2$Cl$_2$ film) 3428, 2961, 1819, 1730, 1177, 1028, 774 cm$^{-1}$; Anal. Calcd for C$_8$H$_{12}$O$_4$: C, 55.81; H, 7.02. Found C, 56.11; H, 7.34.

EXAMPLE 19

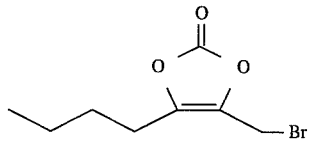

A 0° C. solution of Example 18 alcohol (2.000 g, 11.6 mmol) in CH$_2$Cl$_2$ (150 mL) was treated with carbon tetrabromide (4.616 g) followed by triphenylphosphine (3.347 g). After 30 minutes at 0° C. and 1 hour at room temperature, the mixture was worked-up and flash chromatographed (Merck SiO$_2$, ⅜-EtOAc/hexane as eluant) to provide pure title compound (2.149 g): 79% yield; TLC R$_f$ 0.47 (3:7-EtOAc:hexanes); $^1$H-NMR (CDCl$_3$) δ0.95 (t, 3H, J=7.5 Hz), 1.39 (m, 2H), 1.60 (m, 2H), 2.45 (t, 2H, J=7.5 Hz), 4.19 (s, 2H); $^{13}$C-NMR (CDCl$_3$) δ151.70, 141.58, 134.35, 28.28, 23.55, 21.92, 17.82, 13.55; IR (CH$_2$Cl$_2$ film) 2961, 2874, 1823, 1721, 1225, 1184, 1115 cm$^{-1}$; Anal. Calcd for C$_8$H$_{12}$O$_4$: C, 40.88; H, 4.72; Br, 33.99. Found C, 40.90; H, 4.71; Br, 33.93.

EXAMPLE 20

α-[Bis-[[5-butyl-2-oxo-1,3-dioxol-4-yl]methoxy]phosphinyl]-3-phenoxybenzenebutanesulfonic acid, ammonium salt The Example 4 Part A triacid was azeotroped with EtOAc/toluene and dried in vacuo to give a clear reddish oil.

A solution of the dried triacid (830 mg, 2.15 mmol) and diisopropylethylamine (DIPEA) (1.27 mL) in CH$_3$CN (10 mL) was treated with Example 19 bromide (1.725 g) in CH$_3$CN (8mL). After stirring at room temperature for 5 days, the mixture was worked-up and purified by preparative HPLC to give title compound as a clear gum (925 mg, 61% yield).

Mass spec. (M+NH$_4$)$^+$ @ 712, (M-H)$^+$ @ 693, MW-684
Anal. Calcd for C$_{32}$H$_{39}$O$_{13}$SP•HN$_3$: C, 54.00; H, 5.95; N, 1.87; P, 4.35; S, 4.50 Found: C, 53.78; H, 6.03; N, 2.04; P, 4.40; S, 4.40.

EXAMPLE 21

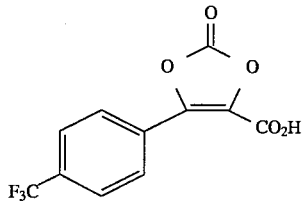

A.

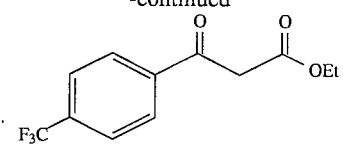

To a stirring suspension of ethyl malonate potassium salt (25.02 g, 147 mmol) in 210 mL of CH$_3$CN cooled at 0° C. was added dropwise Et$_3$N (20.5 mL, 147 mmol) over 15 min. After the suspension was stirred for 15 min, MgCl$_2$ (16.7 g, 175 mmol) was added in one portion. After stirring under argon at room temperature for 2.5 h, the reaction mixture was cooled at 0° C. and p-trifluoromethyl benzoylchloride (10.4 mL, 70 mmol) was added dropwise. After addition, the reaction mixture was stirred at room temperature for 18 h, then concentrated in vacuo. The residue was partitioned between 500 mL of toluene and 100 mL of 10% aqueous HCl. The separated toluene was washed with water (3×), brine, dried (Na$_2$SO$_4$) and filtered. The filtrate was concentrated and the residue adsorbed on Celite, and chromatographed eluting with 10% EtOAc/hexane to afford 10.506 g (58%) of title compound as a light brown oil. R$_f$=0.73 (1:1 EtOAc/hexane); $^1$H-NMR (CDCl$_3$, 400 MHz); Mass Spec: [M+H] 261, MW @ 260.

B.

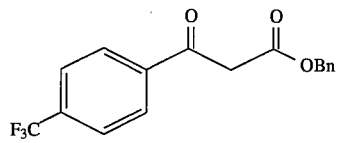

To a solution of Part A compound (10.50 g, 40.38 mmol) in 120 mL of toluene was added benzyl alcohol (42 mL, 404 mmol), followed by DMAP (740 mg, 6.06 mmol). The reaction mixture was refluxed under argon for 24 h before cooling down to room temperature. The mixture was diluted with hexane (400 mL), washed with 5% aqueous KHSO$_4$ (2×), H$_2$O (2×), brine, dried (Na$_2$SO$_4$) and filtered. The filtrate was concentrated first under house vacuum to remove hexane and toluene, then under high vacuum to remove most of the benzyl alcohol. The remaining residue was chromatographed (silica gel column) eluting with 15% EtOAc/hexane to give 12.02 g (92%) of title compound as a light brown oil. $^1$H-NMR (CDCl$_3$, 400 MHz).

C.

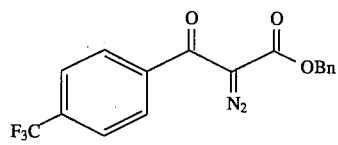

To a solution of Part B compound (11.7 g, 36.4 mmol) and Example 1 Part A sulfonyl azide, (8.92 g, 36.4 mmol) in CH$_3$CN (361 mL) cooled to 0° C. was added triethylamine (14.9 mL, 3 eq.) dropwise. The resultant yellow suspension was stirred at 0° C. for 30 mins, then at room temperature overnight. The reaction mixture was concentrated and triturated with 1:1 ethyl ether:petroleum ether (520 mL). The filtrate was concentrated in vacuo and triturated with 2:1 ethyl ether:petroleum ether (600 mL). The crude product was chromatographed (silica gel column) eluting with 10% EtOAc/hexane and the obtained product recrystallized from hexane to give title compound (9.64 g) in 86% yield. $^1$H NMR and $^{13}$C NMR (CDCl$_3$).

D.

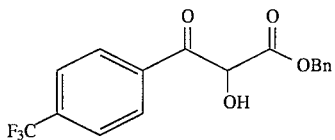

To a solution of Part C compound (9.22 g, 26.4 mmol) in 2:1 THF/water (172 mL) was added rhodium(II) acetate dimer (228 mg, 0.52 mmol) in three portions and the resultant pale green solution was refluxed for 3 hrs. The reaction mixture was concentrated in vacuo and the remaining residue was extracted with EtOAc (2×300 mL). The combined extracts were washed with brine (2×150 mL), and dried over Na$_2$SO$_4$. The filtrate was concentrated in vacuo and the residue recrystallized from 20% methylene chloride in toluene to give title compound (5.7 g) in 64% yield. $^1$H NMR and $^{13}$C NMR (CDCl$_3$).

E.

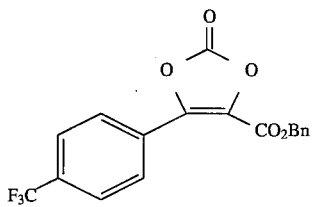

To a solution of Part D compound (5.2 g, 15.43 mmol) and carbonyldiimidazole (5.0 g, 30.86 mmol) in THF (77.2 mL) cooled to 0° C. was added DIPEA (134 μL, 0.77 mmol) dropwise over 5 minutes. The resultant solution was stirred at 0° C. for an additional 20 minutes, then at room temperature overnight. The reaction mixture was concentrated in vacuo and redissolved in EtOAc. The EtOAC was washed with 5% KHSO$_4$, brine, dried over Na$_2$SO$_4$ filtered and concentrated in vacuo. The crude product was purified on a silica gel column eluting with 10% EtOAc in hexanes and the obtained product recrystallized from EtOAc:hexane (1:20) to give title compound (3.75 g) in 67% yield. $^1$H NMR and $^{13}$C NMR (CDCl$_3$).

F.

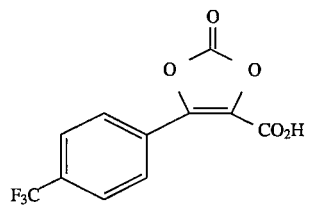

To a solution of Part E compound (3.54 g, 9.72 mmol) in EtOAc:EtOH (1:3) was added Pd(OH)$_2$/C (90 mg) at room temperature. The reaction was hydrogenated under hydrogen balloon for 30 minutes and filtered through a cake of celite. The filtrate was concentrated in vacuo to give title compound (2.6 g) in 98% yield. $^1$H NMR and $^{13}$C NMR (CDCl$_3$).

EXAMPLE 22

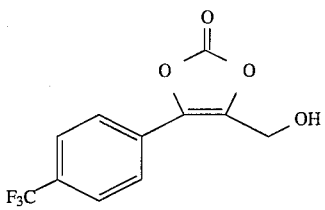

To a suspension of Example 21 acid (1.66 g, 6.05 mmol) in dry CH$_2$Cl$_2$ (16.9 mL) cooled at 0° C. was added DMF (84 μL), followed by oxalyl chloride (634 μl) dropwise over for 15 minutes. The reaction was stirred at 0° C. for 20 minutes until no bubbles were generated and at room temperature for 90 minutes. The reaction mixture was concentrated, then stripped with toluene and dried in vacuo for 30 minutes to give acid chloride.

To a suspension of NaBH$_4$ (458 mg, 12.1 mmol) in anhydrous EtOH (33.8 mL) cooled to −75° C. was added CH$_2$Cl$_2$, (78.8 mL) followed by dropwise addition of acid chloride in dry CH$_2$Cl$_2$ (78.8 mL) over 15 minutes at −73° to −70° C. The reaction mixture was stirred at −74° C. for 2 hrs then placed at −80° C. overnight. The reaction mixture was quenched with 1N HCl (6.7 mL) with vigorous stirring and warmed up to room temperature. The reaction mixture was diluted with 15 mL H$_2$O and 10 mL CH$_2$Cl$_2$ and the layers separated. The aqueous layer was extracted with CH$_2$Cl$_2$ (2×25 mL) and the combined organic layers were washed with brine, and dried over Na$_2$SO$_4$. The filtrate was concentrated in vacuo to give title compound (1.49 g) in 94% yield. $^1$H NMR and $^{13}$C NMR (CDCl$_3$).

EXAMPLE 23

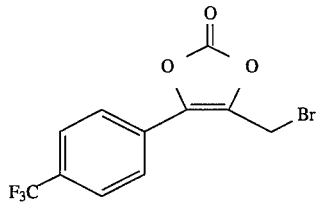

To a solution of Example 22 compound (954 mg, 3.67 mmol) in dry CH$_2$Cl$_2$ (18.4 mL) cooled to 0° C. was added carbon tetrabromide (1.46 g, 4.40 mmol) in one portion followed by triphenylphosphine (1.06 g, 4.04 mmol) in one portion. The reaction mixture was stirred at 0° C. for 10 minutes then at room temperature for 3 minutes until homogeneous. The reaction was stirred again at 0° C. for 30 minutes, adsorbed onto Celite and purified on a silica gel column eluting with 10% EtOAc in hexane to give title compound (603 mg) in 51% yield. $^1$H and $^{13}$C NMR (CDCl$_3$).

HPLC: Rt=20.11 min (EM Lichrosphere select B, C-8, 5μ, 4×250 mm, 28–70% B:A); solvent A: 95% H$_2$O/5% CH$_3$CN+0.01M NH$_4$OAc, pH 5.5; solvent B: 95% CH$_3$CN/ 5% H$_2$O+0.01M NH$_4$OAc, pH 5.5.

EXAMPLE 24

α-[Bis[[2-oxo-5-[4-(trifluoromethyl)phenyl]-1,3-dioxol-4-yl]methoxy]phosphinyl]-3-phenoxybenzenebutanesulfonic acid, potassium salt

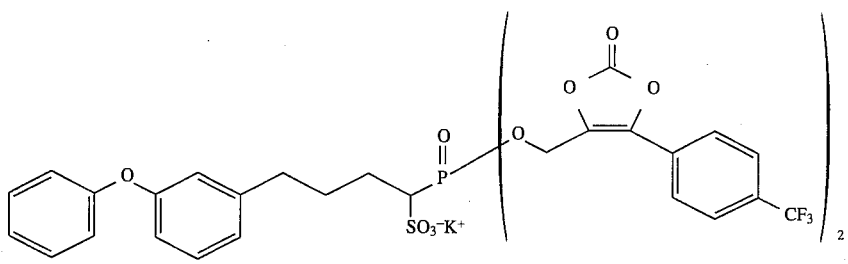

The Example 4 Part A triacid was azeotroped with EtOAc/toluene (2×) and dried in vacuo for one hour to give a clear reddish oil.

To a solution of the triacid (245 mg, 0.64 mmol) in dry CH₃CN (19 mL) was added dropwise diisopropylethylamine (422 μl, 2.42 mmol) followed by dropwise addition of the Example 23 bromide (779 mg, 2.42 mmol). The reaction mixture was stirred at room temperature for 4 days. The reaction was concentrated in vacuo and dissolved in CH₃CN. The crude product was purified by preparative HPLC (seven injections of 250 mg using 2 consecutive EM Merck, RP Select B columns and eluting with 56% isocratic B:A (95% CH₃CN/5% H₂O; A=95% H₂O/5%CH₃CN+ 0.04M NH₄OAc, PH 5.5)) at a rate of 35 mL/minute, detecting at 215 nm. The desired fractions were combined and lyophilyzed to give a white lyophillate which was dissolved in EtOAc. The EtOAC solution was washed with KH₂PO₄ buffer (pH 2) then KH₂PO₄ buffer (pH6) and the combined aqueous layers were back extracted with EtOAc. All the organic layers were combined and washed with saturated KCl and dried over KCl. The filtrate was concentrated in vacuo and lyophilized to give a white oil which was relyophillized to give title compound (235 mg) in 50% yield.

M.S.: (M-H)⁻, @ 869⁻; MW=870

$^{1}$H NMR: (400 MHz/CD₃OD): 7.84–7.72 (m's, 9H), 7.33 (m, 2H), 7.17 (t, 1H, J=6.7), 7.03 (m, 1H), 6.91 (m, 3H), 6.89 (s, 1H), 6.71 (m, 1H), 5.15–5.35 (m's, 4H), 3.48–3.58 (m's, 1H), 3.30 (s, 3H), 2.60 (m, 2H), 1.93–2.25 (m's, 2H), 1.41 (m, 2H).

$^{13}$C NMR: (100 MHz/CD₃OD): 158.8, 158.6, 152.3, 145.4, 141.3, 136.6, 136.3, 133.0, 132.9, 132.7, 132.6, 130.8, 129.2, 127.8, 127.2, 124.5, 124.1, 120.0, 119.7, 117.3, 60.8, 59.3, 59.2, 58.4, 36.4, 30.9, 28.7.

HPLC: Rt=17.01 min (99%, UV 215); EM Lichresphere select B (C-8, 5μ, 4×250 mm); 28%–70%; A: 95% H₂O/5% CH₃CN+0.01M NH₄OAc, pH 5.5; solvent B: 95% CH₃CN/5%H₂O+0.01M NH₄OAc, pH 5.5

Elemental analysis for C₃₈H₂₈O₁₃SPF₃·K·0.6 H₂O: Cal: C, 49.63; H, 3.20; F, 12.40; P, 3.37; S, 3.49 Found: C, 49.63; H, 3.10; F, 12.45; P, 3.54; S, 3.43

What is claimed is:

1. A process for preparing a dioxolenone derivative of the structure

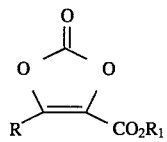
(1)

where R is alkyl or aryl, and R₁ is arylalkyl, H or alkyl, which comprises reacting an ester of the structure

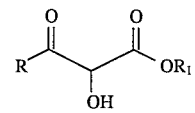

where R and R₁ are as defined above, with an amine base and a cyclizing agent to form a dioxolenone derivative of the structure

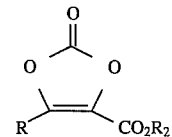

where R₂ is arylalkyl or alkyl, and optionally reducing the above dioxolenone derivative to form the dioxolenone acid derivative of the structure

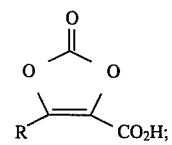

or a process for preparing a dioxolenone derivative of the structure

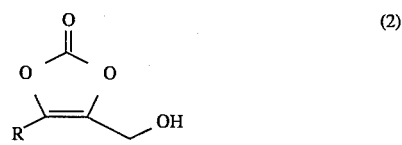
(2)

wherein R is alkyl or aryl, which comprises providing a dioxolenone acid derivative of the structure

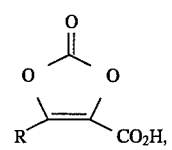

reacting the above dioxolenone acid derivative with a chlorination agent to form the corresponding acid chloride, reducing the acid chloride while cooling at a temperature within the range from about −78° to about 0° C., to form

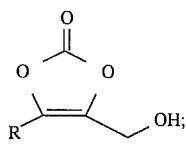

or a process for preparing a dioxolenone derivative of the structure

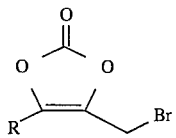 (3)

wherein R is alkyl or aryl, which comprises providing a dioxolenone acid derivative of the structure

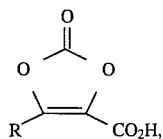

reacting the dioxolenone acid derivative with a chlorination agent to form the corresponding acid chloride, reducing the acid chloride while cooling at a temperature within the range from about −78° to about 0° C. to form the dioxolenone derivative

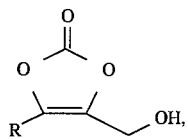

reacting the above dioxolenone derivative with a bromination agent and a dehydrating agent to form

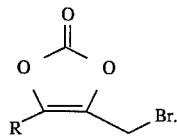

2. The process as defined in claim 1 wherein the cyclizing agent in (1) is phosgene or a phosgene equivalent which is diphosgene, triphosgene or 1,1'-carbonyldiimidazole.

3. The process as defined in claim 1 wherein the amine base in (1) employed is diisopropylethylamine, triethylamine, N-methylmorpholine or pyridine.

4. The process as defined in claim 1 where in the starting ester R is isopropyl, ethyl, t-butyl, n-propyl, n-butyl or p-trifluoromethylphenyl and $R_1$ is benzyl.

5. The process as defined in claim 1 wherein the chlorination agent in (2) is oxalyl chloride, thionyl chloride or phosphorus trichloride.

6. The process as defined in claim 1 wherein the reducing agent in (2) is tetrabutylammonium borohydride, lithium tri-tert-butoxyaluminohydride or sodium borohydride.

7. The process as defined in claim 1 wherein the chlorination agent in (3) is oxalyl chloride, thionyl chloride or phosphorus trichloride.

8. The process as defined in claim 1 wherein the bromination agent is carbon tetrabromide, phosphorus tribromide or bromine, and the activating agent (3) is triphenylphosphine, tributylphosphine or triphenylphosphite.

9. The process as defined in claim 1 wherein the reducing agent (3) is tetrabutylammonium borohydride, lithium tri-tert-butoxyaluminohydride or sodium borohydride.

10. The process as defined in claim 1 wherein the starting alcohol

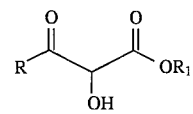

is prepared by reacting a compound of the structure

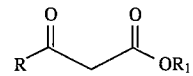

with a sulfonyl azide of the structure

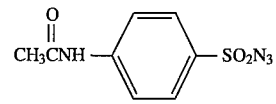

in the presence of an amine base to form a α-diazo β-keto ester of the structure

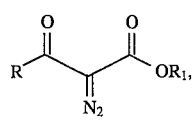

treating the α-diazo β-keto ester with a catalytic amount of a catalyst which is

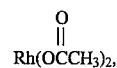

copper(metal) or copper chloride, at a temperature within the range of from about 40° to about 100° C. to form the starting alcohol.

11. The process as defined in claim 10 wherein the α-diazo β-keto ester is treated with catalytic amounts of rhodium (II) acetate dimer.

* * * * *